US012557983B2

(12) United States Patent
Kang et al.

(10) Patent No.: US 12,557,983 B2
(45) Date of Patent: Feb. 24, 2026

(54) DEVICE AND METHOD FOR PROVIDING VISUAL PERCEPTION TRAINING USING VISUAL PERCEPTION LEARNING

(71) Applicant: NUNAPS INC., Seoul (KR)

(72) Inventors: Dong Wha Kang, Seoul (KR); Rak Kyeun Hong, Guri-si (KR)

(73) Assignee: Nunaps Inc., Seoul (KR)

( * ) Notice: Subject to any disclaimer, the term of this patent is extended or adjusted under 35 U.S.C. 154(b) by 473 days.

(21) Appl. No.: 18/153,121

(22) Filed: Jan. 11, 2023

(65) Prior Publication Data

US 2023/0165461 A1 Jun. 1, 2023

Related U.S. Application Data

(63) Continuation of application No. PCT/KR2021/003254, filed on Mar. 16, 2021.

(30) Foreign Application Priority Data

| Jul. 16, 2020 | (KR) | 10-2020-0088439 |
| Jul. 16, 2020 | (KR) | 10-2020-0088441 |
| Jul. 16, 2020 | (KR) | 10-2020-0088442 |

(51) Int. Cl.
A61B 3/024 (2006.01)
A61B 3/00 (2006.01)
(Continued)

(52) U.S. Cl.
CPC ............ A61B 3/024 (2013.01); A61B 3/0091 (2013.01); A61B 3/02 (2013.01); A61B 3/028 (2013.01);
(Continued)

(58) Field of Classification Search
CPC ......... A61B 3/0091; A61B 3/02; A61B 3/024; A61B 3/028; A61B 3/032; A61B 3/113;
(Continued)

(56) References Cited

U.S. PATENT DOCUMENTS

| 6,527,391 B1 * | 3/2003 | Heijl ...................... A61B 3/024 |
| | | 351/243 |
| 9,940,844 B2 | 4/2018 | Gazzaley |

(Continued)

FOREIGN PATENT DOCUMENTS

| JP | 5466188 B2 | 4/2014 |
| JP | 6666938 B2 | 3/2020 |

(Continued)

OTHER PUBLICATIONS

An Office Action mailed by the Korean Intellectual Property Office on Apr. 27, 2023, which corresponds to Korean Patent Application No. 10-2020-0088439 and is related to U.S. Appl. No. 18/153,121.

(Continued)

*Primary Examiner* — Jason M Mandeville
(74) *Attorney, Agent, or Firm* — Studebaker Brackett PLLC

(57) ABSTRACT

Disclosed is a device for providing visual perception training including a display module, and a controller for acquiring at least one target area corresponding to at least one of a first cell of a left eye visual field map and a second cell of a right eye visual field map, and providing a visual perception task to the at least one target area. In the providing of the visual perception task, the controller displays, through the display module, a task object for receiving a response of a patient and fixing a central visual field of the patient, displays, through the display module, at least one stimulus object at at least one stimulus position corresponding to the at least one target area, and acquires the response of the patient related to the task object.

15 Claims, 28 Drawing Sheets

(51) Int. Cl.

| | |
|---|---|
| *A61B 3/02* | (2006.01) |
| *A61B 3/028* | (2006.01) |
| *A61B 3/113* | (2006.01) |
| *A61B 5/16* | (2006.01) |
| *A61H 5/00* | (2006.01) |
| *G09B 21/00* | (2006.01) |
| *A61B 3/032* | (2006.01) |

(52) U.S. Cl.
CPC .............. *A61B 3/113* (2013.01); *A61B 5/163* (2017.08); *A61H 5/00* (2013.01); *G09B 21/007* (2013.01); *A61B 3/032* (2013.01); *A61H 2201/5043* (2013.01)

(58) Field of Classification Search
CPC ..... A61B 5/1103; A61B 5/163; G09B 21/007; A61H 2201/5043; A61H 5/00
USPC ........................................................ 351/158
See application file for complete search history.

(56) References Cited

U.S. PATENT DOCUMENTS

| | | | |
|---|---|---|---|
| 2006/0283466 A1 | 12/2006 | Sabel | |
| 2007/0182928 A1* | 8/2007 | Sabel | A61B 3/024 |
| | | | 351/224 |
| 2007/0216865 A1* | 9/2007 | Sabel | A61H 5/00 |
| | | | 351/203 |
| 2010/0118264 A1 | 5/2010 | Sabel | |
| 2012/0127426 A1* | 5/2012 | Backus | A61H 5/005 |
| | | | 351/203 |
| 2012/0208170 A1 | 8/2012 | Kimura et al. | |

| | | | |
|---|---|---|---|
| 2013/0201452 A1* | 8/2013 | Crabb | A61B 3/024 |
| | | | 351/224 |
| 2014/0370479 A1 | 12/2014 | Gazzaley | |
| 2015/0282704 A1* | 10/2015 | Maddess | A61B 3/024 |
| | | | 600/558 |
| 2017/0035317 A1* | 2/2017 | Jung | A61B 3/0025 |
| 2017/0296774 A1 | 10/2017 | Acton | |
| 2018/0055433 A1* | 3/2018 | Ally | A61B 5/16 |
| 2018/0261115 A1 | 9/2018 | Gazzaley | |
| 2019/0269315 A1* | 9/2019 | Lu | G16H 50/20 |
| 2020/0073476 A1* | 3/2020 | Tiwari | A61B 3/024 |

FOREIGN PATENT DOCUMENTS

| | | |
|---|---|---|
| KR | 10-1242162 B1 | 3/2013 |
| KR | 10-2015-0118242 A | 10/2015 |
| KR | 10-1984995 B1 | 5/2019 |
| KR | 10-1965393 B1 | 8/2019 |

OTHER PUBLICATIONS

The extended European search report issued by the European Patent Office on Jul. 5, 2024, which corresponds to European Patent Application No. 21842375.4-1122 and is related to U.S. Appl. No. 18/153,121.

International Search Report issued in PCT/KR2021/003254; mailed Jun. 30, 2021.

Communication pursuant to Article 94(3) EPC issued by the European Patent Office on Mar. 27, 2025, which corresponds to European Patent Application No. 21 842 375.4-1122 and is related to U.S. Appl. No. 18/153,121.

* cited by examiner

FIG. 3

| Type | Example | | | | | |
|---|---|---|---|---|---|---|
| Figure | ● | ⬤ | ◯ | ▲ | ■ | |
| Gabor | G1 | G2 | G3 | G4 | G5 | G6 |
| Text | ㄱ | ㅌ | A | T | a | |

FIG. 6

| | | -2 | -20 | -18 | -23 | | |
|---|---|---|---|---|---|---|---|
| | -18 | -11 | -4 | -7 | -1 | -6 | |
| -17 | -17 | -6 | -4 | -4 | -3 | -1 | -4 |
| -22 | -21 | -4 | -7 | -4 | -3 | -1 | -1 |
| -27 | -27 | -13 | -9 | -6 | -12 | -9 | -30 |
| | -28 | -15 | -6 | -8 | -20 | -11 | -11 | -29 |
| | | -29 | -30 | -17 | -30 | -14 | -19 |
| | | -28 | -29 | -30 | -29 | | |

1102

8

7

First time point                    Second time point

DEVICE AND METHOD FOR PROVIDING VISUAL PERCEPTION TRAINING USING VISUAL PERCEPTION LEARNING

CROSS-REFERENCE TO RELATED APPLICATIONS

The present application is a continuation of International Patent Application No. PCT/KR2021/003254, filed on Mar. 16, 2021, which is based upon and claims the benefit of priority to Korean Patent Application Nos. 10-2020-0088439 filed on Jul. 16, 2020, 10-2020-0088441 filed on Jul. 16, 2020 and 10-2020-0088442 filed on Jul. 16, 2020. The disclosures of the above-listed applications are hereby incorporated by reference herein in their entirety.

BACKGROUND

Embodiments of the inventive concept described herein relate to a device and method for providing visual perception training to improve a visual ability, and more particularly, relate to a device and method for providing visual perception training to improve a visual ability by using visual perception learning.

Many patients experience discomfort due to a visual field disorder or impaired visual ability caused by eye diseases such as glaucoma, macular degeneration, and diabetic retinopathy. The eye diseases may cause abnormalities in a visual system, such as a problem in a function of an optic nerve due to pressure on the optic nerve or failure of blood supply.

In the past, drugs have been injected or surgery has been performed to treat these diseases, but may not be cured.

Accordingly, there is continuously required for an effective method for improving a visual ability. A device and method for improving such the visual ability by performing visual perception learning has emerged.

SUMMARY

Embodiments of the inventive concept provide improving a visual ability by using visual perception learning.

Embodiments of the inventive concept provide training to patients suffering from a visual field disorder by using visual perception learning.

Embodiments of the inventive concept providing patients with efficient visual perception learning.

Problems to be solved are not limited to the above-described problem, and other problems not mentioned herein may be clearly understood from this specification and the accompanying drawings by those skilled in the art to which the inventive concept pertains.

According to an embodiment, a device for providing visual perception training including a display module, and a controller for acquiring at least one target area corresponding to at least one of a first cell of a left eye visual field map and a second cell of a right eye visual field map, and providing a visual perception task to the at least one target area. In the providing of the visual perception task, the controller displays, through the display module, a task object for receiving a response of a patient and fixing a central visual field of the patient, displays, through the display module, at least one stimulus object at at least one stimulus position corresponding to the at least one target area, and acquires the response of the patient related to the task object. The at least one stimulus position is positioned at a periphery of the task object, and the visual field map includes a vision index for reflecting the visual field disorder of the patient.

Moreover, the display module may include a left display unit and a right display unit. The controller may display the at least one stimulus object at the at least one stimulus position corresponding to the first cell through the left display unit and may display the at least one stimulus object at the at least one stimulus position corresponding to the second cell through the right display unit.

Furthermore, the controller may provide the patient with a visual perception task by displaying the task object during a specific time through the display module and may display a stimulus object during only a partial time of the specific time.

Besides, the at least one stimulus object may include a first stimulus object output at a first time point and a second stimulus object output at a second time point different from the first time point.

Also, at least one of the task object and the at least one stimulus object may be a gabor.

In addition, the at least one stimulus object may be a gabor having a spatial frequency of 0.1 to 1 cycle/degree.

Moreover, the at least one stimulus object may be output while flickering at a predetermined temporal frequency, and the temporal frequency may be 10 to 50 Hz.

Furthermore, the response of the patient may be associated with an attribute of the task object.

Besides, the attribute may include at least one of a rotation direction and pattern orientation of the task object.

According to an embodiment, a method for improving a visual ability by using visual perception learning includes acquiring at least one target area corresponding to at least one of a first cell of a left eye visual field map and a second cell of a right eye visual field map, and providing a visual perception task based on the at least one target area. The providing of the visual perception task includes displaying a task object for receiving a response of a patient and fixing a central visual field of the patient, displaying at least one stimulus object at at least one stimulus position corresponding to the at least one target area; and acquiring the response of the patient related to the task object. The at least one stimulus position is positioned at a periphery of the task object, and the visual field map includes a vision index for reflecting the visual field disorder of the patient.

Solutions to the problem are not limited to the above-described solution, and solutions not mentioned herein may be clearly understood from this specification and the accompanying drawings by those skilled in the art to which the inventive concept pertains.

BRIEF DESCRIPTION OF THE FIGURES

The above and other objects and features will become apparent from the following description with reference to the following figures, wherein like reference numerals refer to like parts throughout the various figures unless otherwise specified, and wherein:

FIG. 3 is a diagram of a non-limiting example of a visual object, according to an embodiment of the inventive concept;

FIG. 6 is a diagram of a visual field map including a plurality of cells, to which a vision score is assigned, according to an embodiment of the inventive concept;

DETAILED DESCRIPTION

Figure 1:
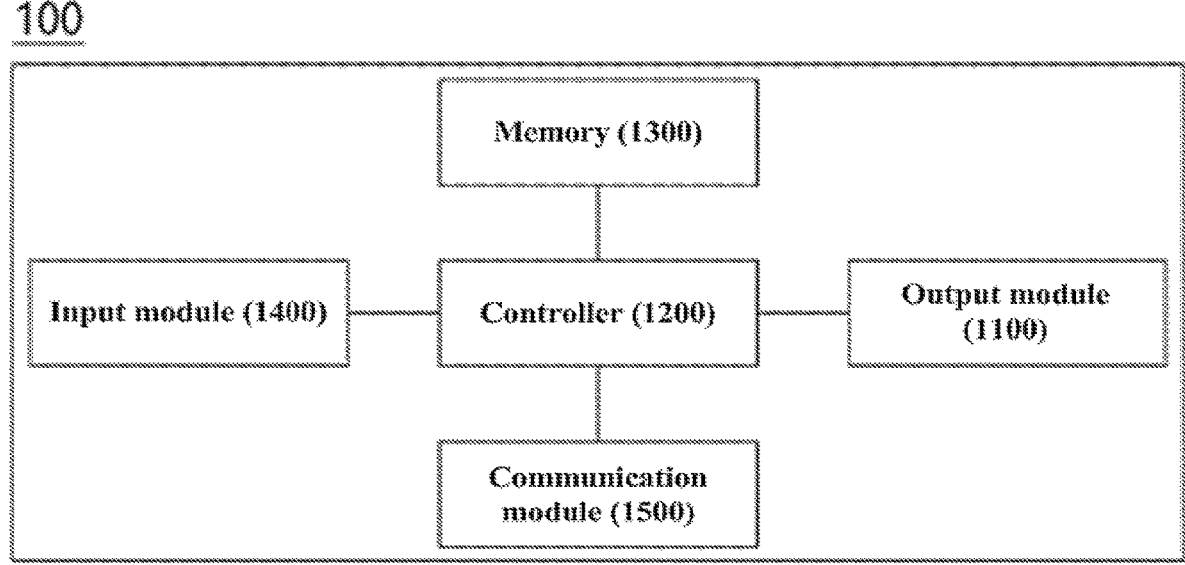
FIG. 1 is a diagram for describing a visual perception training providing device, according to an embodiment of the inventive concept.

The above and other aspects, features and advantages of the inventive concept will become apparent from embodiments to be described in detail in conjunction with the accompanying drawings. The inventive concept, however, may be embodied in various different forms, and should not be construed as being limited only to the illustrated embodiments. Rather, these embodiments are provided as examples so that the inventive concept will be thorough and complete, and will fully convey the scope of the inventive concept to those skilled in the art. The inventive concept may be defined by the scope of the claims.

The terms used herein are provided to describe embodiments, not intended to limit the inventive concept. In the specification, the singular forms include plural forms unless particularly mentioned. The terms "comprises" and/or "comprising" used herein do not exclude the presence or addition of one or more other components, in addition to the aforementioned components. The same reference numerals denote the same components throughout the specification. As used herein, the term "and/or" includes each of the associated components and all combinations of one or more of the associated components. It will be understood that, although the terms "first", "second", etc., may be used herein to describe various components, these components should not be limited by these terms. These terms are only used to distinguish one component from another component. Thus, a first component that is discussed below could be termed a second component without departing from the technical idea of the inventive concept.

A word "exemplary" is used herein in the sense of "being used as an example or illustration". An embodiment described herein as "exemplary" is not necessarily to be construed as preferred or advantageous over other embodiments.

The term "unit" used herein may refer to software or hardware such as field programmable gate array (FPGA) or application specific integrated circuit (ASIC), and the "unit" may perform some functions. However, the "unit" may be not limited to software or hardware. The "unit" may be configured to exist in an addressable storage medium or may be configured to play one or more processors. Therefore, as an example, "units" may include various elements such as software elements, object-oriented software elements, class elements, and task elements, processes, functions, attributes, procedures, subroutines, program code segments, drivers, firmware, microcodes, circuits, data, databases, data structures, tables, arrays, and variables. Functions provided in "units" and elements may be combined into a smaller number of "units" and elements or may be divided into additional "units" and elements.

Moreover, in this specification, all "units" may be controlled by at least one processor, and at least one processor may perform operations performed by the "units" of the inventive concept.

Embodiments of the present specification may be described in terms of a function or a block performing a function. A block capable of being referred to as a 'unit' or a 'module' of the inventive concept is physically implemented by analog or digital circuits such as logic gates, integrated circuits, microprocessors, microcontrollers, memories, passive electronic components, active electronic components, optical components, hardwired circuits, and the like and may be selectively driven by firmware and software.

Embodiments of the present specification may be implemented by using at least one software program running on at least one hardware device and may perform a network management function of controlling an element.

Unless otherwise defined, all terms (including technical and scientific terms) used herein have the same meaning as commonly understood by those skilled in the art to which the inventive concept pertains. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein.

As illustrated in the figures, spatially relative terms, such as "below", "beneath", "lower", "above", "upper", and the like, may be used herein for ease of description to describe the relationship between one component and other components. It will be understood that the spatially relative terms are intended to encompass different orientations of the components in use or operation in addition to the orientation depicted in the figures. For example, when inverting a component shown in the figures, a component described as "below" or "beneath" of another component may be placed "above" another element. Thus, the exemplary term "below" may include both downward and upward directions. The components may also be oriented in different directions, and thus the spatially relative terms may be interpreted depending on orientation.

In this specification, perceptual learning refers to learning for improving the perception of a stimulus through repetitive training on the stimulus. In other words, in this specification, visual perception learning refers to learning for improving the perception of a visual stimulus through repetitive training with a visual stimulus. As a result of the visual perception learning, learners may see things they couldn't see before or may notice differences they couldn't distinguish before. In addition to learning for improving the ability to find objects from a stimulus that comes from the outside through a visual organ, the visual perception learning should be broadly interpreted to include learning for improving the ability to discriminate objects from the stimulus.

In this specification, a visual field defect/visual field disorder refers to the disorder of a visual system from a retina to a cerebral cortex or the abnormality of a visual field. For example, the visual field defect should be broadly interpreted to include not only a visual field defect due to a brain function damage but also a visual field defect due to the death (or malfunction) of a retinal ganglion cell. Non-limiting examples of diseases that cause the visual field disorder may include glaucoma, macular degeneration, diabetic retinopathy, hemianopia, and quadrantanopia.

In this specification, in addition to vision measured based on whether letters, numbers, or symbols on an eyesight test chart may be identified in order of size, the visual ability should be broadly interpreted as a concept that includes a visual perception ability related to object recognition in a brain. For example, eyes normally accept visual stimuli. However, an object is not perceived because the brain fails to perceive the visual stimulus. This may mean that the visual ability is degraded or bad.

In this specification, expression "training" means an action for improving or beneficially changing symptoms of the visual field defect/visual field disorder. As a non-limiting example, training may be a measure for obtaining effects such as inhibiting the progression of the visual field defect, reducing the progression rate of the visual field defect, stopping the progression of the visual field defect, and improving the visual field defect.

In this specification, an expression "task" may refer to a goal and/or objective to be achieved by a user. For example, a computerized task may be rendered by using computerized components, and a user may receive instructions regarding the goal or objective for performing the computerized task. The task may allow an individual to provide or withhold a response to a specific stimulus.

In this specification, an expression "session" may refer to a time period having a start and an end, at each of which a user interacts with a device to receive learning from the device. For example, a session may have 1 second, 30 seconds, 1 minute, 1 hour, 12 hours, a day, a week, a month, and the like.

In this specification, a visual object may mean a visual stimulus such as a visual object output to the user. A detailed embodiment of the visual object will be described later.

Hereinafter, a visual perception training providing device for improving a visual ability by using visual perception learning will be described.

FIG. 1 is a diagram for describing a visual perception training providing device, according to an embodiment of the inventive concept.

Referring to FIG. 1, a visual perception training providing device 100 according to an embodiment may include an output module 1100, a controller 1200, a memory 1300, an input module 1400, and a communication module 1500.

The visual perception training providing device 100 may include various devices capable of performing calculation processing. For example, the visual perception training providing device 100 may include a desktop PC, a mobile phone, a smart phone, a laptop computer, personal digital assistants (PDA), a portable multimedia player (PMP), a slate PC, a tablet PC, an ultrabook, a wearable device, and the like.

According to an embodiment, the visual perception training providing device 100 may be worn on a part of a body, and may be used in a manner in which the output module 1100 and a user's eyes face each other. For example, the visual perception training providing device 100 may include a head mounted display (HMD) mounted on the user's head to display an image, a head-mounted device such as smart glasses and smart goggles, or a display device of a mobile phone capable of being mounted and used on the HMD.

The output module 1100 may output a video or an image. For example, the output module 1100 may include an LCD, an OLED display, an AMOLED display, and the like. Here, when the output module 1100 is provided as a touch screen, the output module 1100 may perform a function of the input module 1400. In this case, the separate input module 1400 may not be provided depending on a selection, and the input module 1400 performing limited functions such as a volume control button, a power button, and a home button may be provided. For another example, the output module 1100 may be provided in a form of a video output port that transmits video information to an external display device.

According to an embodiment, a screen of the output module 1100 may include a left display unit corresponding to a patient's left eye and a right display unit corresponding to the patient's right eye. Here, the left display unit may output a first image, and the right display unit may output a second image. The controller 1200 may adjust the disparity or focus of an image provided to a user by adjusting a distance between the first image and the second image, an overlapping degree, and the like. The first image and the second image may be the same image as each other or may be images at least partially overlapping each other. Alternatively, the first image and the second image may be images that do not overlap each other.

Moreover, the left display unit and the right display unit may be physically separated display modules from each other. Alternatively, the left display unit and the right display unit may be a left area and a right area of the same display module, respectively.

Furthermore, the output module 1100 may display an image for a user's visual perception learning. For example, the output module 1100 may visually output a process before a visual perception task is started, an instruction, an image for performing a visual perception task, and the like.

Moreover, the output module 1100 may output information to be provided to the user in various manners. For example, the output module 1100 may include a speaker, a motor, a haptic device, a vibrator, a signal output circuit, and the like, and may be a module that outputs various stimuli.

In addition, the output module 1100 may audibly or tactilely output information for a visual perception task. In detail, the output module 1100 may audibly or tactilely output an alarm indicating the start and end of a training session.

According to an embodiment, the output module 1100 may output a stimulus for other perceptual learning (e.g., auditory perception learning). As a non-limiting example, the output module 1100 may output an auditory stimulus for auditory perception learning. In detail, the output module 1100 may output an instruction for providing a notification of rules related to an auditory perception task, an auditory stimulus for the auditory perception task, and the like.

The controller 1200 may control each component of the visual perception training providing device 100 or may process and calculate various types of information. For example, the controller 1200 may output an image for a visual perception task through the output module 1100. In detail, the controller 1200 may determine a position of a visual object on the output module 1100 in a visual perception task based on the acquired visual field map of the user, and then may display a visual object at a position determined through the output module 1100.

The controller 1200 may be implemented with software, hardware, or a combination thereof. For example, in a hardware manner, the controller 1200 may be implemented with a field programmable gate array (FPGA) or an application specific integrated circuit (ASIC), a semiconductor chip, or other various types of electronic circuits. Also, for example, in a software manner, the controller 1200 may be implemented with a logic program executed depending on the above-described hardware or various computer languages.

Unless otherwise stated in the following description, it may be understood that an operation of the visual perception training providing device 100 is performed under the control of the controller 1200.

The memory 1300 may store various pieces of data. For example, the memory 1300 may store data related to a visual perception task. In detail, the memory 1300 may store a program for executing a visual perception task, user information (e.g., a user's personal information, information related to the visual perception task, the user's response when a task is performed, and the user's visual perception task result), and data related to a user's visual field map.

Moreover, the memory 1300 may include a storage medium of at least one type of a flash memory type, a hard disk type, a multimedia card micro type, a card type memory (e.g., SD memory, XD memory, etc.), a random access memory (RAM), a static random access memory (SRAM), a read-only memory (ROM), an electrically erasable programmable read-only memory (EEPROM), a programmable read-only memory (PROM), a magnetic memory, a magnetic disk, an optical disc, etc. Besides, the memory 1300 may store information temporarily, permanently, or semi-permanently, and may be provided in an embedded type or a removable type.

The input module 1400 may obtain a signal corresponding to a user's input. For example, the input module 1400 may receive a user input for performing the visual perception task, a user input for adjusting the focus of the image for the visual perception task during visual perception learning, and a user input for receiving the user's response requested by the visual perception task, and the like.

Moreover, the input module 1400 may include a keyboard, a keypad, a button, a jog shuttle, a wheel, and the like. Besides, the user's input in the input module 1400 may be, for example, pressing a button, touching, and dragging. Furthermore, when the output module 1100 is implemented as a touch screen, the output module 1100 may serve as the input module 1400.

According to an embodiment, the input module 1400 may be configured as a separate module connected to the visual perception training providing device 100 in a wired or wireless manner. For example, the visual perception training providing device 100 may provide the user with images for a visual perception task through the output module 1100 mounted on the user's head, and may receive an input for the visual perception task from the user through the input module 1400 composed of a separate module given to the user's hand.

The communication module 1500 may communicate with an external device. For example, the communication module 1500 may communicate with a server. In detail, the communication module 1500 may transmit data related to the user's visual perception task to the server, and may receive personalized feedback on the data from the server.

Also, the communication module 1500 may perform communication according to wired and wireless communication standards. For example, the communication module 1500 may include Bluetooth Low Energy (BLE), Bluetooth, Wireless LAN (WLAN), Wireless Fidelity (WiFi), WiFi Direct, Near Field Communication (NFC), Infrared Data Association (IrDA).

A mobile communication module including Ultra Wide Band (UWB), Zigbee, 3G, 4G, or 5G, and a wired/wireless module for transmitting data through various other communication standards may be also included.

Figure 2:
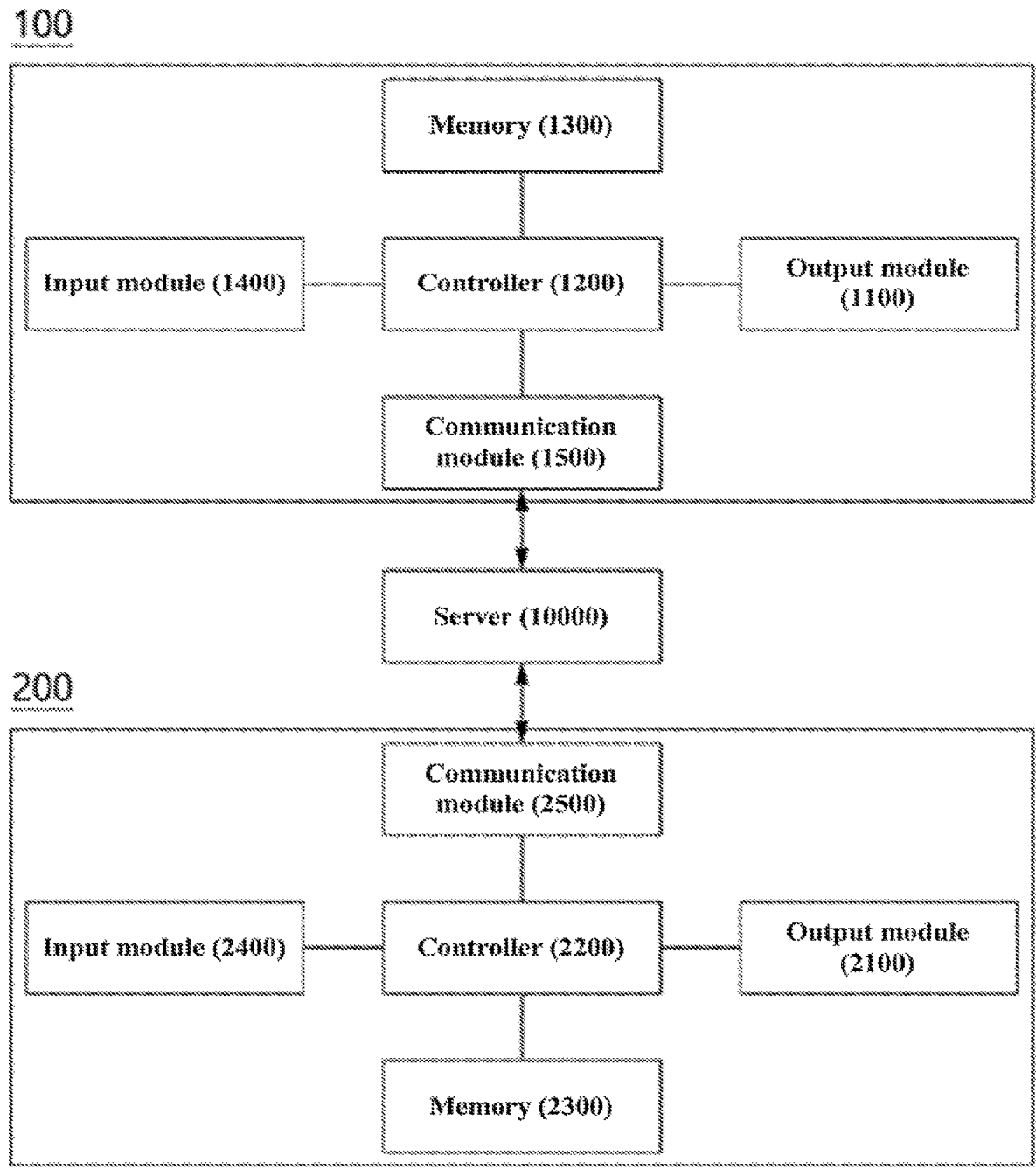
FIG. 2 is a diagram for describing a visual perception training providing device that communicates with a server, according to an embodiment of the inventive concept.

FIG. 2 is a diagram for describing a visual perception training providing device that communicates with a server, according to an embodiment of the inventive concept.

Referring to FIG. 2, devices 100 and 200 according to an embodiment may communicate with a server 10000 by receiving or transmitting data from or to the server 10000 through communication modules 1500 and 2500. For example, the server 10000 may receive or transmit, from or to the devices 100 and 200, instructions, an image for performing a visual perception task, a program for performing the visual perception task, a user's personal information, information about the visual perception task, the user's response upon performing a task, a result of the user's visual perception task, and data related to the user's visual field map.

The visual perception training providing devices 100 and 200 shown in FIGS. 1 and 2 are only examples, and configurations of the devices 100 and 200 are not limited thereto. For example, a function performed by each configuration of the visual perception training providing devices 100 and 200 is not necessarily performed by the corresponding component, but may be performed by another configuration. For example, it may be described that memories 1300 and 2300 of the visual perception training providing devices 100 and 200 store data related to the user's visual perception task. However, the server 10000 connected to the visual perception training providing devices 100 and 200 through the communication modules 1500 and 2500 may store data related to the user's visual perception task.

Hereinafter, a method for improving a visual ability by using visual perception learning is described.

According to an embodiment, the method for improving a visual ability by using visual perception learning may provide the user with a visual perception task including a visual object by using a visual perception training providing device to treat/improve a user/patient's visual impairment or disease.

The visual object may be provided to the user through an output module.

FIG. 3 is a diagram of a non-limiting example of a visual object, according to an embodiment of the inventive concept.

Referring to FIG. 3, the type of a visual object may include a figure type, a gabor type, and a text type.

The visual object may have various attributes such as a type, a size, a shape, a color, saturation, brightness, movement, a pattern orientation, a spatial frequency of a pattern, a phase of the pattern, a temporal frequency, and contrast.

Here, the spatial frequency of a pattern may be a frequency, at which the pattern is repeated in a space, and may be expressed, for example, in units of cycle/degree. The spatial frequency may be 0.1 to 1 cycle/degree. Alternatively, the spatial frequency may be 0.5 cycle/degree.

Moreover, the temporal frequency is a frequency, at which the visual object flickers, and may be expressed, for example, in units of Hz. The temporal frequency may be 10 to 50 Hz. Alternatively, the temporal frequency may be 18 to 30 Hz. Alternatively, the temporal frequency may be 20 Hz. As the visual object is output while flickering, the improvement effect of a visual ability or visual field disorder may increase.

The visual object may have a shape type. Referring to FIG. 3, the visual object may have a circle, triangle, or rectangle, and other various shapes.

Furthermore, the visual object may have a filled figure, a figure with only a border, or a partially filled figure.

The visual object may have a gabor type. Referring to FIG. 3, the visual object of a gabor type may have various changeable attributes such as a size of a gabor, an orientation of a pattern, a spatial frequency of the pattern, a temporal frequency, a phase of the pattern, and contrast. For example, a size of a first gabor G1 may be greater than a size of a second gabor G2. Alternatively, a pattern orientation (a vertical direction) of the first gabor G1 may be different from a pattern orientation (a diagonal direction) of a third gabor G3. Alternatively, a spatial frequency of the pattern of the first gabor G1 may be smaller than a spatial frequency of the pattern of a fourth gabor G4. Alternatively, a phase of the pattern of the first gabor G1 may be different from a phase of the pattern of a fifth gabor G5. Alternatively, the contrast of the first gabor G1 may be greater than the contrast of a sixth gabor G6.

The visual object may have a text type. Referring to FIG. 3, the visual object may be Korean consonants or vowels such as 'ㄱ' and 'ㅌ'. Alternatively, the visual object may be an English uppercase letter such as 'A' or 'T' or a lowercase letter such as 'a'. Besides, the visual object may be various characters.

The color, saturation, and brightness of the visual object may vary. For example, the visual object may have the color, saturation, or brightness that induces an increase in optic nerve stimuli.

The visual object may have motion attributes indicating a movement or rotation. For example, the visual object may rotate in a specific direction. Alternatively, depending on a phase change of a gabor pattern, the user may recognize that a gabor is rotating. As another example, depending on a change in the size of the visual object, the user may recognize that the visual object is moving as if it is approaching or moving away.

The visual object may include a central fixation object for the user's central fixation. The central fixation object may be output in a central area of an output module, but is not limited thereto. For example, the central fixation object may be output at a position where the user's central gaze is to be fixed on the output module.

The visual object may include a central object output in a central area of the output module, and a peripheral object output in a periphery of the central object depending on an output position in the output module.

Figure 4:
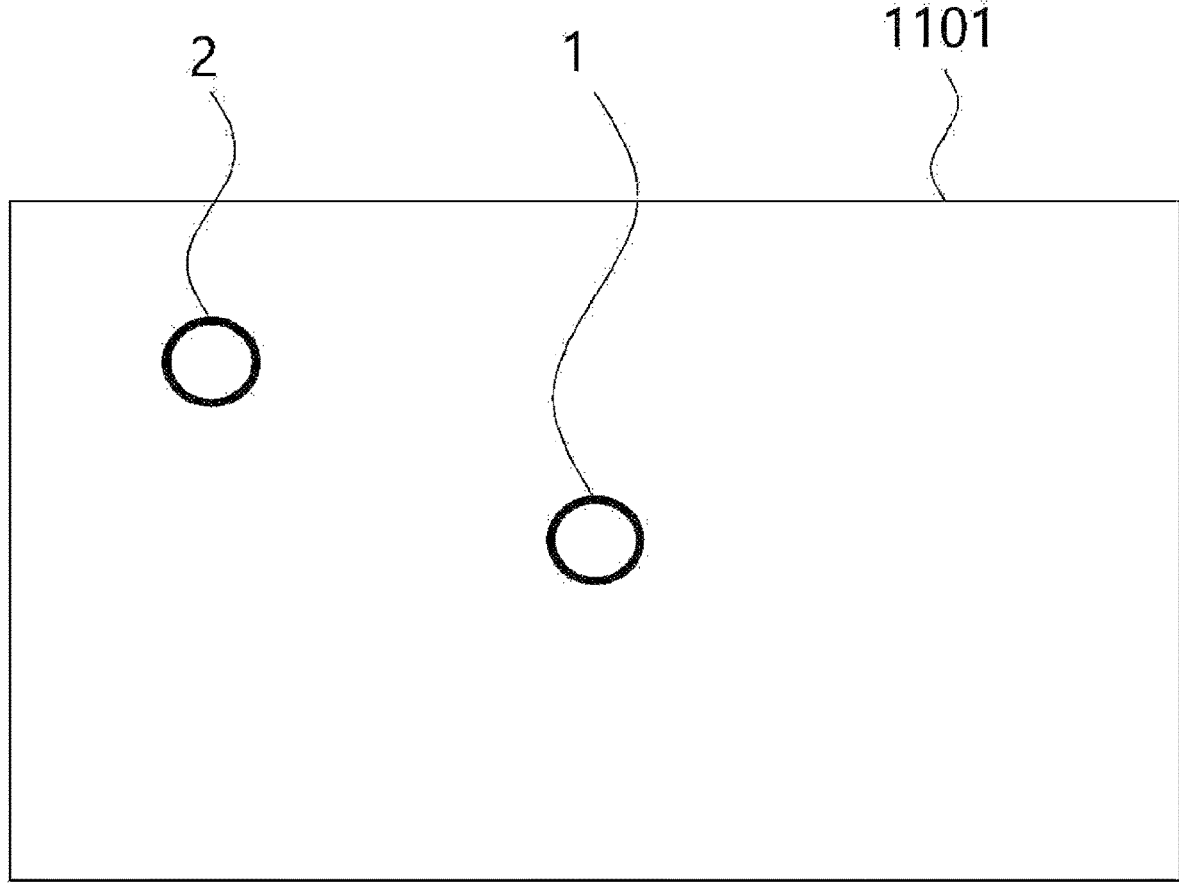
FIG. 4 is a diagram for describing classification according to an output position of a visual object, according to an embodiment of the inventive concept.

FIG. 4 is a diagram for describing classification according to an output position of a visual object, according to an embodiment of the inventive concept.

Referring to FIG. 4, a visual object may include a central object 1 and a peripheral object 2 output to the central area of an output module 1101. Here, the central object 1 may correspond to a central fixation object, but is not limited thereto.

The visual object may include a task object relevant to a user reaction and a stimulus object not relevant to the user reaction. The user may determine the user reaction based on only the task object. Here, the user reaction is a user's response to a visual perception task or visual object, and includes not only the case where the user enters a user input into a device through an input module, but also the case where the user does not respond intentionally (e.g. the case where the user does not enter a user input intentionally). The stimulus object may be output to a position corresponding to a visual field defect area that is not related to the user reaction but requires visual field disorder treatment. In addition, the task object may also be output to a position corresponding to a visual field defect area. The task object may be a central fixation object, but is not limited thereto. The task object may be a central object, and the stimulus object may be a peripheral object, but is not limited thereto. For example, each of the task object and the stimulus object may be at least one of a central object and a peripheral object.

Figure 5:
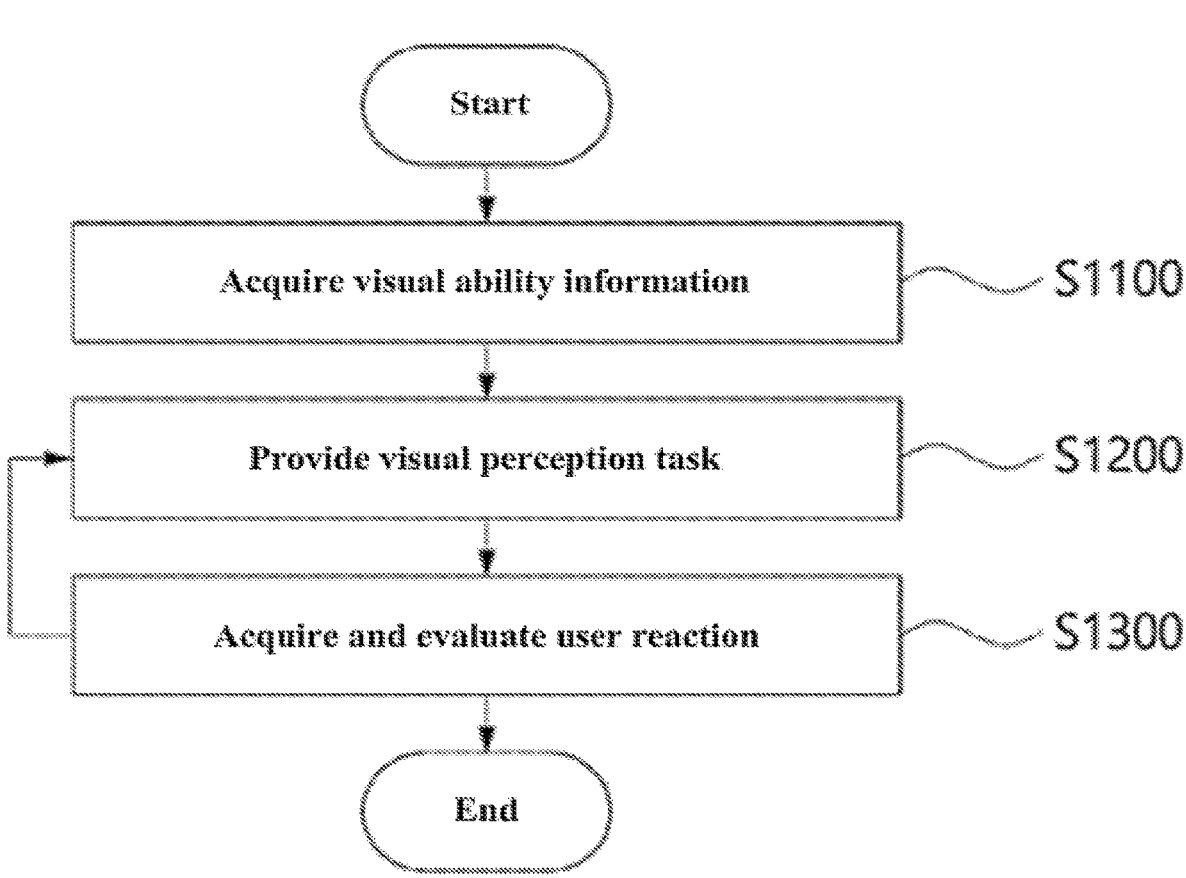
FIG. 5 is a flowchart illustrating a method for improving a visual ability by using visual perception learning, according to an embodiment of the inventive concept.

FIG. 5 is a flowchart illustrating a method for improving a visual ability by using visual perception learning, according to an embodiment of the inventive concept. Referring to FIG. 5, a method may include acquiring visual ability information (S1100), providing a visual perception task (S1200), and acquiring and evaluating a user reaction (S1300). According to an embodiment, the method may be used to improve the defect/damage of a specific visual field area of a user/patient. Hereinafter, a visual field area where training for a patient having a visual field disorder is performed, or a visual field area where training is mainly performed is referred to as a "target area". For example, a visual field damage area may be the target area. Moreover, a position on an output module corresponding to the target area is referred to as a "target position". Furthermore, a cell of a visual field map corresponding to the target area on a visual field map to be described later is referred to as a "target cell".

The acquiring of the visual ability information (S1100) according to an embodiment may include acquiring information related to a visual ability of a user/patient. For example, a device may acquire visual ability information of the user/patient. Here, the visual ability information may be a visual field test result obtained through a visual field test such as perimetry.

The visual ability information according to an embodiment may be a visual field map. Here, the visual field map is a map that indicates the user's visual field range and visual ability. For example, the visual field map may include a plurality of cells to which vision indices reflecting the user's visual ability are assigned.

A specific cell of the visual field map may correspond to the user's specific visual field area.

For example, a first cell and the second cell of the visual field map may correspond to a first visual field area and a second visual field area, respectively. Alternatively, a cell located in a center of the visual field map may correspond to a central visual field area, and a cell located in a periphery may correspond to a peripheral visual field area. Alternatively, a cell located at a lower part of the visual field map may correspond to a lower visual field area, and a cell located at an upper part may correspond to an upper visual field area.

The vision index may mean a scale indicating the degree of a visual ability of the user (or the degree of disease progression).

According to an embodiment, the vision index may be a vision score that is a value within a predetermined numerical range. As the vision score is high, it is indicated that the visual ability of the corresponding cell is good. On the other hand, as the vision score is low, it is indicated that the visual ability of the corresponding cell is good.

FIG. 6 is a diagram of a visual field map including a plurality of cells, to which a vision score is assigned, according to an embodiment of the inventive concept.

Referring to FIG. 6, a vision score may be assigned to a cell. For example, the vision score may have an integer value of −30 or more and 0 or less. As a value is great, it is indicated that the visual ability is good. A visual field map may include a cell to which a vision score is not assigned.

The cell to which the vision score is not assigned may be a cell corresponding to a blind spot. Hereinafter, unless otherwise noted for convenience of description, as a value has an integer value of −30 or more and 0 or less and is great, the vision score indicates that a visual ability is good. However, an embodiment is not limited thereto.

According to another embodiment, the vision index may be a vision status expressing the degree of a user's visual ability as a grade. For example, the user's visual ability may be expressed as a normal status corresponding to a normal visual ability and a vision status of a visual field defect status corresponding to an abnormal visual ability or visual field defect. Alternatively, the user's visual ability may be expressed as a vision status including a normal status, a dead status where it is difficult to recover the visual ability due to severe visual ability damages, and a dysfunctional status which has visual ability damages but which the visual ability is capable of being recovered. Besides, the vision status may be expressed as various grades.

Figure 7:
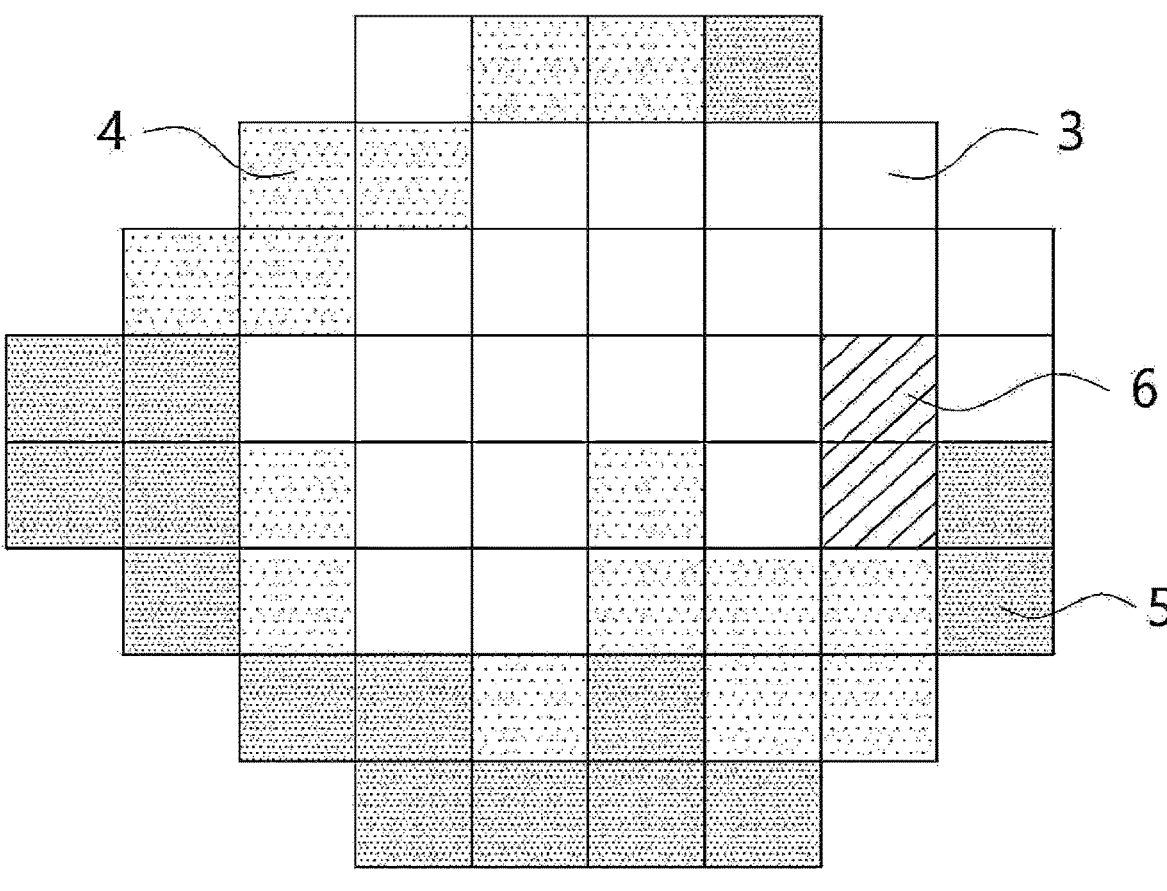
FIG. 7 is a diagram of a visual field map including a plurality of cells, to each of which a vision status is assigned, according to an embodiment of the inventive concept.

FIG. 7 is a diagram of a visual field map including a plurality of cells, to each of which a vision status is assigned, according to an embodiment of the inventive concept.

Referring to FIG. 7, a visual field map may include a cell 3 (hereinafter referred to as a "normal cell"), to which a vision status being a normal status is assigned, a cell 4 (hereinafter referred to as a "dysfunctional cell"), to which a vision status being a dysfunctional status is assigned, and a cell 5 (hereinafter referred to as a "dead cell"), to which a vision status being a dead status is assigned. The visual field map may include a cell to which a vision status is not assigned. The cell to which a vision status is not assigned may be a cell corresponding to a blind spot. In FIG. 7, for convenience of description, different vision statuses are expressed as different patterns. Hereinafter, unless otherwise noted for convenience of description, it is described based on a vision status including a normal status, a dysfunctional status, and a dead status, but is not limited thereto.

The vision status may be determined based on a vision score. For example, the visual field map to which a vision status is assigned may be generated based on the vision score. Alternatively, the visual field map to which vision status is assigned may be generated based on the visual field map to which the vision score is assigned.

According to an embodiment, the vision status may be determined based on a numerical range of the vision score. For example, vision scores of a first numerical range and a second numerical range may correspond to vision statuses of a first status and a second status, respectively. Referring to FIGS. 6 and 7, a vision score of −10 or more and 0 or less may correspond to a vision status being a normal status; a vision score of −20 or more and −11 or less may correspond to a vision status being a dysfunctional status; and, a vision score of −30 or more and −21 or less may correspond to the vision status being a dead status. The correspondence relationship between the vision score and the vision status in FIGS. 6 and 7 is an example, and the correspondence relationship is not limited thereto.

According to an embodiment, the providing of the visual perception task (S1200) may include providing a visual perception task to a user/patient. According to another embodiment, the providing of the visual perception task (S1200) may include outputting a visual object.

The visual perception task may be provided based on visual ability information. Here, the visual ability information may be visual ability information acquired in the acquiring of the visual ability information (S1100) or visual ability information generated/updated in the acquiring and evaluating of the user reaction (S1300), which will be described later. Alternatively, the visual perception task may be provided based on the evaluation result calculated in the acquiring and evaluating of the user reaction (S1300), which will be described later.

The visual object may be output at a specific position of an output module. The output position of a visual object may mean a position where the visual object is displayed on an output module. The visual object may be output at a position on the output module corresponding to the target area.

The specific position of the output module may correspond to a specific cell of a visual field map. For example, a first position and a second position of the output module may correspond to a first cell and a second cell of the visual field map, respectively. The specific position of the output module may correspond to a user's specific visual field area. For example, the first position and the second position of the output module may correspond to a first visual field area and a second visual field area, respectively. Alternatively, the center of the output module may correspond to a central visual field area, and the periphery may correspond to a peripheral visual field area. Alternatively, a lower part of the output module may correspond to a lower visual field area and an upper part thereof may correspond to an upper visual field area.

The visual object may be displayed at a specific frequency. The visual object may be output to a specific position of an output module at a specific frequency. For example, a frequency at which a visual object is output at the first position of the output module may be different from a frequency at which the visual object is output at the second position of the output module. Alternatively, a frequency at which the visual object is displayed at a target position may be different from a frequency at which the visual object is displayed at another position. Alternatively, the visual object may be displayed at a higher frequency at the target position.

The visual object is displayed in a specific order. Here, the fact that an output order of the visual object is the same may mean that the visual object is output at the same time point. The fact that an output order of the visual object is different may mean that the visual object is output at a different time point.

The visual object may be output with a specific attribute. For example, a visual object displayed at a target position may have an attribute for providing a stronger stimulus than a visual object displayed at another position. The attribute of the visual object is described above, and thus the description thereof will be omitted to avoid redundancy.

Figure 8:
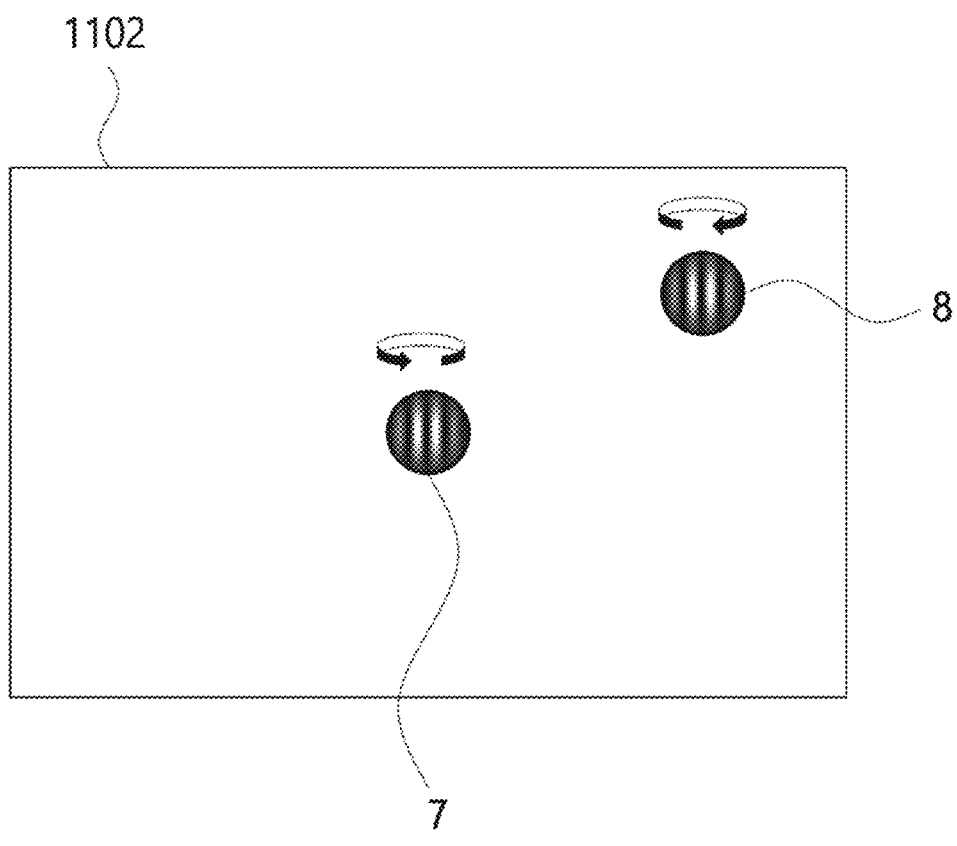
FIG. 8 is a diagram of examples of a visual perception task, according to an embodiment of the inventive concept.
Figure 9:
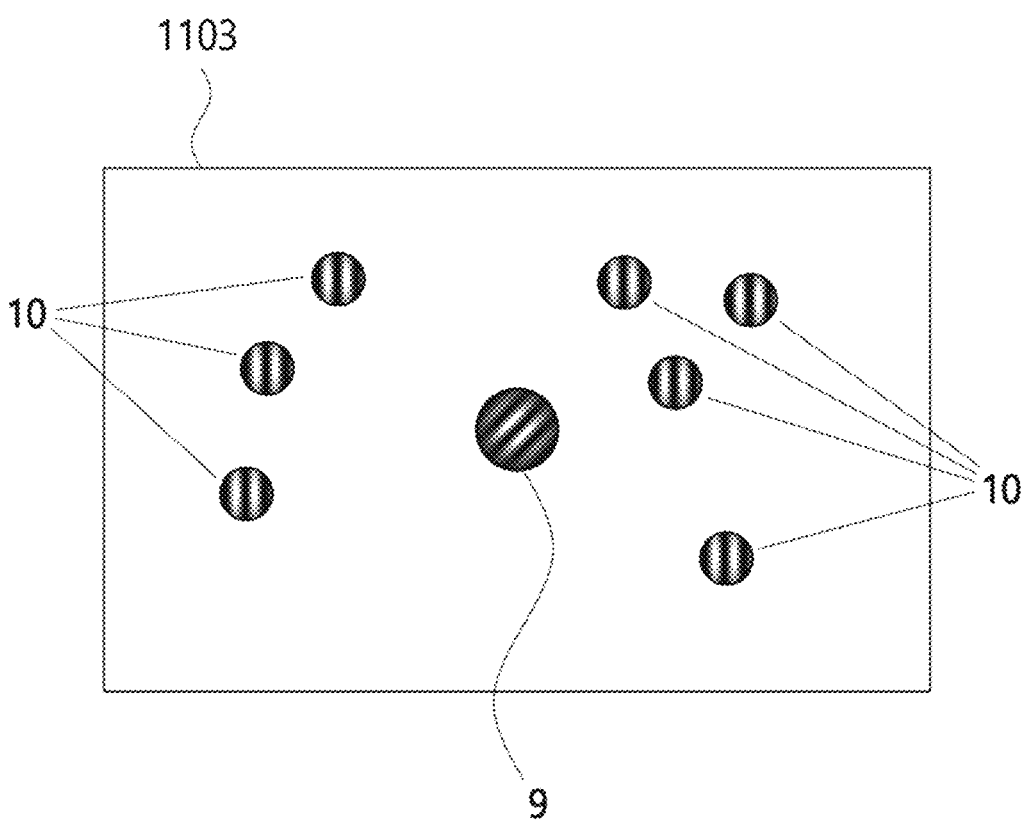
FIG. 9 is a diagram of examples of a visual perception task, according to an embodiment of the inventive concept.

FIGS. 8 and 9 are diagrams of examples of a visual perception task, according to an embodiment of the inventive concept.

Referring to FIG. 8, a device may provide a visual perception task to a user by displaying visual objects 7 and 8 through an output module 1102.

Here, the visual perception task may be used to determine whether attributes of the first visual object 7 and the second visual object 8 are matched with each other. For example, as illustrated in FIG. 8, the visual perception task may be used to determine whether rotational directions of the first visual object 7 and the second visual object 8 of a gabor type are matched with each other. As another example, the visual perception task may be to determine whether the pattern orientations of the first visual object and the second visual object of the gabor type are matched with each other.

The user may determine a user reaction based on whether the attributes of the first visual object and the second visual object are matched with each other. For example, referring to FIG. 8, the rotational directions of the first visual object 7 and the second visual object 8 are different from each other, and thus the user will need to perform a reaction corresponding to the attribute mismatch.

In a case of FIG. 8, both the first visual object 7 and the second visual object 8 are objects relate to the user reaction, and thus the first visual object 7 and the second visual object 8 may be referred to as "task objects". Moreover, the first visual object 7 is referred to as a "central object". The second visual object 8 is referred to as a "peripheral object". Furthermore, one of the first visual object 7 and the second visual object 8 may be a central fixation object.

Next, referring to FIG. 9, a device may provide a visual perception task to a user by displaying visual objects 9 and 10 through an output module 1103. Here, the visual perception task may be used to determine attributes of the third visual object 9. For example, the visual perception task may be used to determine a pattern orientation of the third visual object 9 of the gabor type. Alternatively, the visual perception task may be used to determine the rotational direction of the third visual object.

The user may determine a user reaction based on the attributes of the third visual object 9. For example, when the pattern of the third visual object 9 has a vertical direction, the user needs to perform a first reaction; when the pattern of the third visual object 9 has a horizontal direction, the user needs to perform a second reaction; and, when the pattern of the third visual object 9 has a diagonal direction, the user needs to perform a third reaction. In this case, the third visual object 9 may be referred to as a "task object". Because the fourth visual object 10 has nothing to do with a user reaction, the fourth visual object 10 may be referred to as a "stimulus object". Furthermore, the third visual object 9 may be referred to as a "central object". The fourth visual object 10 may be referred to as a "peripheral object". Also, the third visual object 9 may be a central fixation object. As only the third visual object 9 being the central fixation object is a task object, the user's visual field may be more fixed to the third visual object 9, and thus the central fixation effect may be increased. The fourth visual object 10 may be output while flickering at a specific temporal frequency.

The visual perception task described above with reference to FIGS. 8 and 9 is only an example. In a different manner, a visual perception task may be provided to the user.

Figure 10:
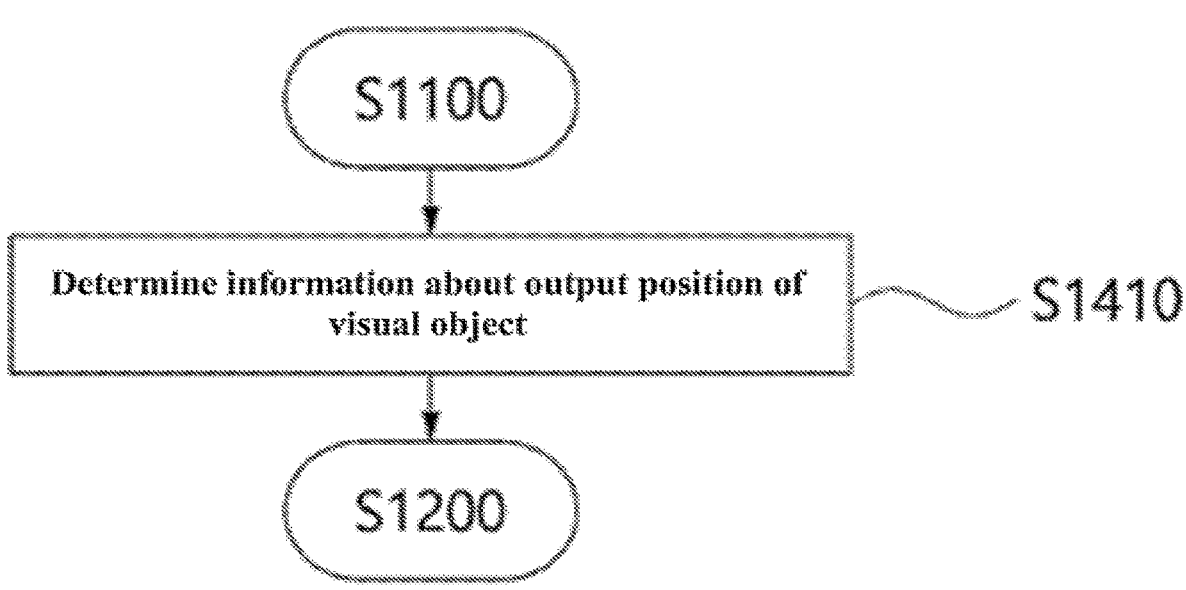
FIG. 10 is a flowchart for describing determining information about an output position of a visual object, according to an embodiment of the inventive concept.

FIG. 10 is a flowchart for describing determining information about an output position of a visual object, according to an embodiment of the inventive concept.

Referring to FIG. 10, according to an embodiment, a method for improving a visual ability by using visual perception learning may include determining information about an output position of a visual object (S1410). According to an embodiment, the determining of the information about the output position of the visual object (S1410) may include determining a target position.

The output position of a visual object may be determined based on a visual ability. For example, the visual object may be output to a position corresponding to a visual field defect area. Alternatively, a position corresponding to the visual field defect area may be a target position. Referring to FIG. 8, the second visual object 8 may be output to a position corresponding to the visual field defect area. Referring to FIG. 9, the fourth visual object 10 may be output to a position corresponding to the visual field defect area.

An output position of a visual object may be determined based on visual ability information such as a visual field map.

An output position of a visual object may be determined based on a vision index.

An output position of a visual object may be determined based on a vision score. For example, a visual object may be displayed at a position corresponding to a cell to which a vision score included in a specific numerical range is assigned. Referring to FIG. 8, the second visual object 8 may be displayed at a position corresponding to a cell to which a vision score included in a specific numerical range is assigned. Referring to FIG. 9, the fourth visual object 10 may be displayed at a position corresponding to a cell to which a vision score included in a specific numerical range is assigned.

The output position of the visual object may be determined based on the vision status. For example, a visual object may be displayed at a position corresponding to a dysfunctional cell. Referring to FIG. 8, the second visual object 8 may be displayed at a position corresponding to a dysfunctional area. Referring to FIG. 9, the fourth visual object 10 may be displayed at a position corresponding to the dysfunctional area.

Whether a visual object is output to a specific position on the output module may be expressed based on a weight corresponding to each output position of an output module. For example, a weight having a first value indicating the output of the visual object may correspond to a first position where the visual object is output. Besides, a weight having a second value of indicating that no visual object is output may correspond to a remaining position.

Figure 11:
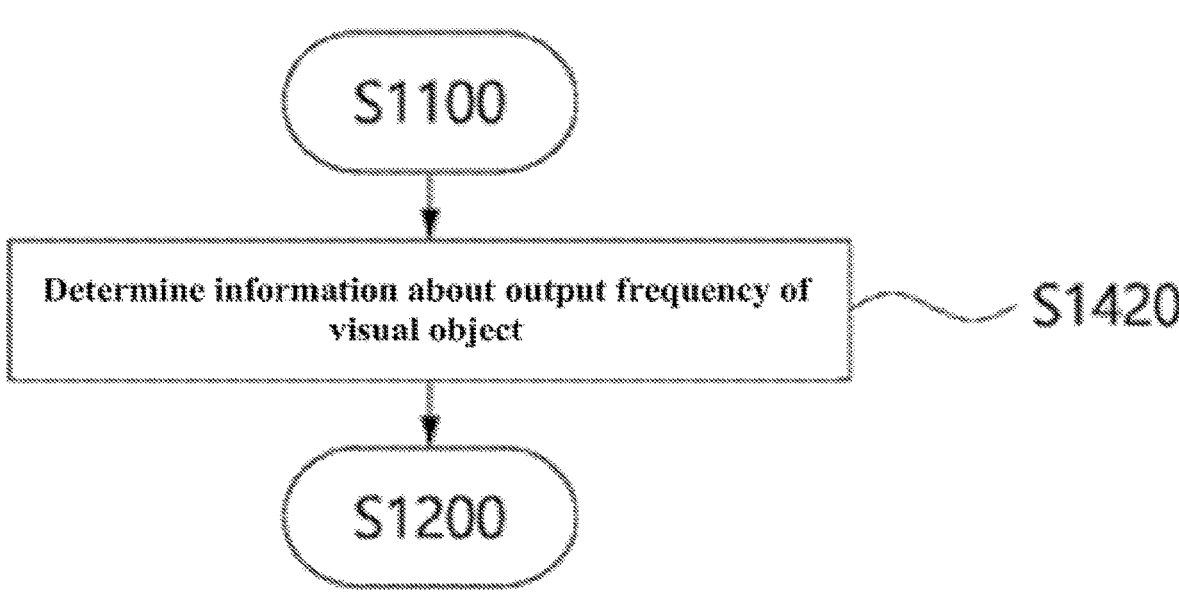
FIG. 11 is a flowchart for describing determining information about an output frequency of a visual object, according to an embodiment of the inventive concept.

FIG. 11 is a flowchart for describing determining information about an output frequency of a visual object, according to an embodiment of the inventive concept.

Referring to FIG. 11, according to an embodiment, a method for improving a visual ability by using visual perception learning may include determining information about an output frequency of a visual object (S1420).

The determining of the information about the output frequency of the visual object (S1420) may include determining an output frequency corresponding to a target position.

The output frequency of a visual object may be determined based on a visual ability. For example, a visual object may be output to a position corresponding to a visual field defect area at a higher frequency than a frequency at a position corresponding to a normal area. Alternatively, the visual object may be output at a high frequency to a position corresponding to an area where a visual ability is relatively low.

An output frequency of the visual object may be determined based on visual ability information such as a visual field map.

The output frequency of the visual object may be determined based on a vision index.

The output frequency of the visual object may be determined based on a vision score. For example, as in the case that an output frequency at a position corresponding to a cell having a vision score of −30 is greater than an output frequency at a position corresponding to a cell having a vision score of −20, the visual object may be output at a high output frequency as the vision score is low. Alternatively, an output frequency at a position corresponding to a cell to which a vision score included in a specific range is assigned may be greater than an output frequency at a position corresponding to the remaining cells. For example, an output frequency at a position corresponding to a cell to which a vision score having −30 or more and −21 or less is assigned may be greater than an output frequency at a position corresponding to the remaining cells. As another example, an output frequency at a position corresponding to a cell to which a vision score having −20 or more and −11 or less is assigned may be greater than an output frequency at a position corresponding to the remaining cells.

The output frequency of a visual object may be determined based on a vision status. For example, an output frequency of a visual object at a position corresponding to a dysfunctional cell may be greater than an output frequency at a position corresponding to other cells.

A frequency at which a visual object is output at a specific position on an output module may be expressed based on a weight corresponding to each output position of the output module. For example, a weight having a first value indicating an output at the first frequency of the visual object and a weight having a second value indicating an output at the second frequency of the visual object may correspond to a first position and a second position on the output module, respectively In this specification, for convenience of description, it is described that the output frequency is high as a weight is great, but is not limited thereto. It is indicated that the output frequency is high as a weight is small.

The visual field disorder treatment effect may vary depending on the output frequency of the visual object. For example, the visual field improvement degree of a visual field area corresponding to a position where the output frequency of the visual object is high may be higher than the visual field improvement degree of the other areas.

The visual object may be displayed at specific time intervals. For example, the visual object may be output during a specific time interval. Afterward, the visual object may not output during a specific time interval and then may output again during a specific time interval.

The visual object may include a visual object, which is temporally continuously output, and a visual object that is discontinuously output. For example, some visual objects may be displayed temporally continuously, and the other visual objects may be output discontinuously.

Figure 12:
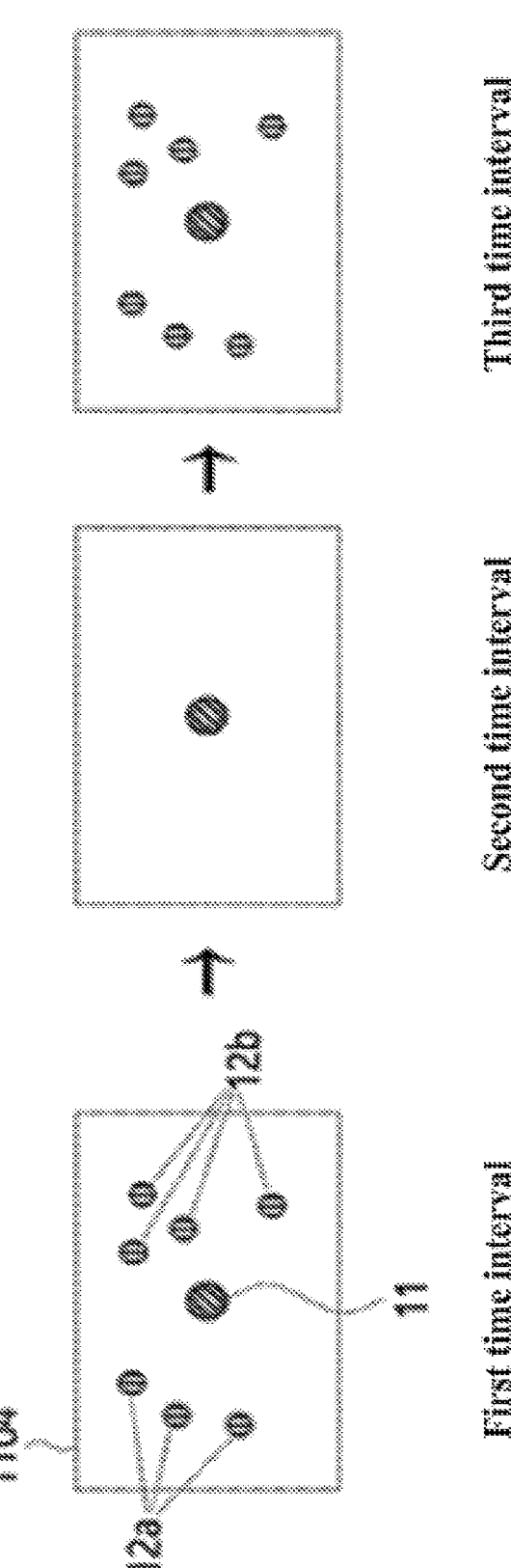
FIG. 12 is a diagram of a visual object output at specific time intervals, according to an embodiment of the inventive concept.

FIG. 12 is a diagram of a visual object output at specific time intervals, according to an embodiment of the inventive concept.

Referring to FIG. 12, a third visual object 11 may be continuously output during a first time interval, a second time interval, and a third time interval. On the other hand, fourth visual objects 12*a* and 12*b* may be output during the first time interval, may not output during the second time interval, and may output again during the third time interval.

As the visual object is output at a specific time interval, the visual field improvement effect may increase. For example, referring to FIG. 12, as compared to the case where the fourth visual objects 12*a* and 12*b* are output continuously during the first time interval, the second time interval, and the third time interval, the visual field improvement effect of a visual field area corresponding to a position where the fourth visual objects 12*a* and 12*b* are output may increase as the fourth visual objects 12*a* and 12*b* are not displayed during the second time interval.

Figure 13:
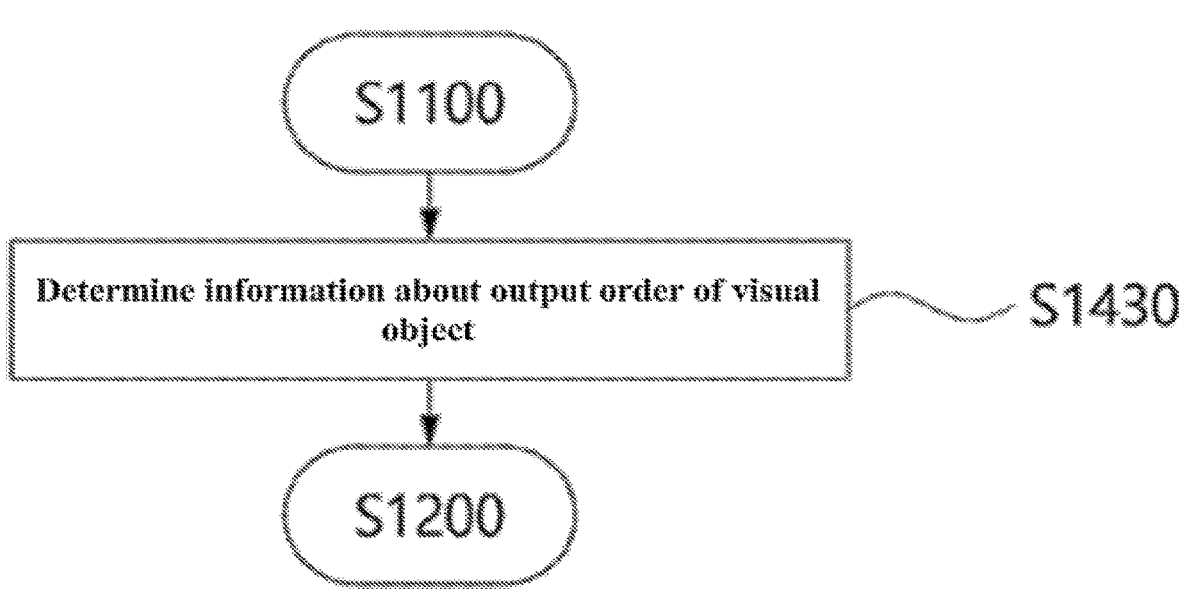
FIG. 13 is a flowchart for describing determining information about an output order of a visual object, according to an embodiment of the inventive concept.

FIG. 13 is a flowchart for describing determining information about an output order of a visual object, according to an embodiment of the inventive concept.

Referring to FIG. 13, according to an embodiment, a method for improving a visual ability by using visual perception learning may include determining information about an output order of a visual object (S1430). According to an embodiment, the determining of the information about the output order of the visual object (S1430) may include determining the output order of visual objects output at a target position.

The visual objects may be output at the same time point. For example, referring to FIG. 9, all of the fourth visual objects 10 may be output at the same time point.

The visual objects may be displayed at different time points from one another. For example, some of the visual objects may be output at the first time point and the others thereof may be output at the second time point.

Figure 14:
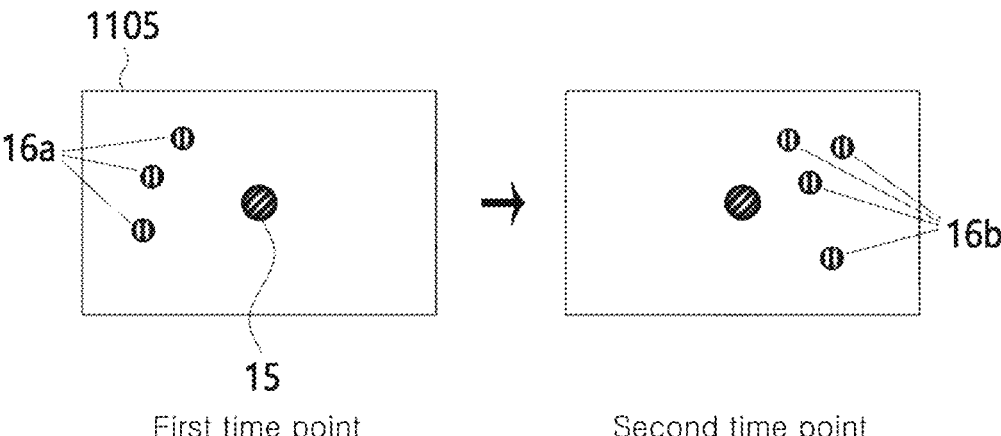
FIG. 14 is a diagram for describing visual objects output at different time points, according to an embodiment of the inventive concept.

FIG. 14 is a diagram for describing visual objects output at different time points, according to an embodiment of the inventive concept.

Referring to FIG. 14, portions 16a of the fourth visual object is first output at the first time point. Afterward, the rest 16b of the fourth visual object may be output at the second time point.

The output order of visual objects may be determined based on output positions of the visual objects. As a non-limiting example, referring to FIG. 14, the portions 16a of fourth visual objects may be first output to a left portion of an output module 1105. After that, the rest 16b of the fourth visual objects may be output on a right side of the output module 1105.

The output order of visual objects may be determined based on a visual ability. The output order of visual objects may be determined based on visual ability information such as a visual field map. The output order of visual objects may be determined based on a vision index. The output order of visual objects may be determined based on a vision score. The output order of visual objects may be determined based on a vision status.

An order in which visual objects are output on the output module may be expressed based on a weight corresponding to each output position of the output module. For example, a weight having a first value indicating an output of the visual object in a first order, and a weight having a second value indicating an output of the visual object in a second order may correspond to a first position and a second position on the output module, respectively FIG. 15 is a flowchart for describing determining information about an attribute of a visual object, according to an embodiment of the inventive concept.

Figure 15:
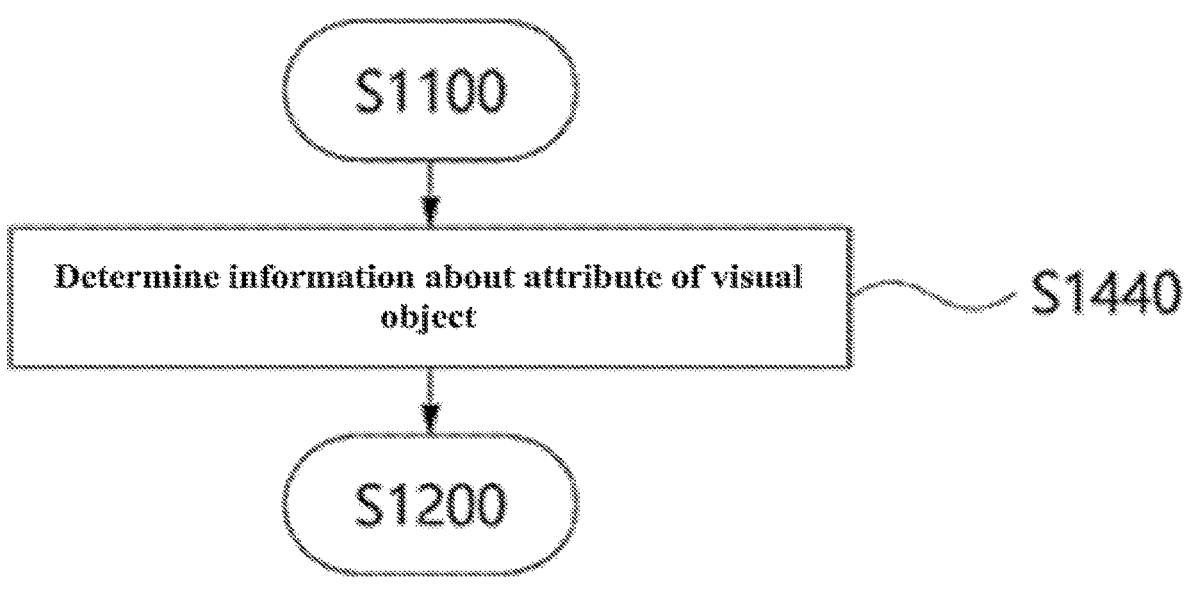
FIG. 15 is a flowchart for describing determining information about an attribute of a visual object, according to an embodiment of the inventive concept.

Referring to FIG. 15, according to an embodiment, a method for improving a visual ability by using visual perception learning may include determining information about an attribute of a visual object (S1440). According to an embodiment, the determining of the information about the attribute of the visual object (S1440) may include determining information about the attribute of the visual object output at a target position.

The attribute of the visual object may be determined based on a visual ability.

For example, the attribute of a visual object output to a position corresponding to a visual field defect area may be different from the attribute of a visual object output to a position corresponding to a normal area. Alternatively, the attribute of a visual object output to a position corresponding to the visual field defect area may be determined to provide a stronger stimulus than the visual object output to a position corresponding to a normal area.

The attribute of the visual object may be determined based on visual ability information such as a visual field map.

The attribute of the visual object may be determined based on a vision index. Moreover, the attribute of the visual object may be determined based on a vision score.

For example, an attribute of a visual object displayed at a position corresponding to a cell to which a first vision score is assigned may be different from an attribute of a visual object displayed at a position corresponding to a cell to which a second vision score is assigned. Alternatively, the attribute of the visual object may be determined to provide a stronger stimulus to a position corresponding to a cell assigned a lower vision score compared to another position.

The attribute of the visual object may be determined based on a vision status. For example, an attribute of a visual object displayed at a position corresponding to a dysfunctional cell may be different from an attribute of a visual object displayed at another position. Alternatively, the attribute of the visual object may be determined to provide a stronger stimulus to a position corresponding to a dysfunctional cell compared to another position.

The attribute of the visual object may be customized for each user. For example, in a case of the visual object of a gabor type, a size of a gabor, an orientation of a pattern, a spatial frequency of the pattern, a phase of the pattern, or contrast may be changed or optimized for each user. Here, the customization may be performed based on a vision index. Alternatively, the customization may be performed in consideration of demographic characteristics such as gender and age of a user, and medical and family history such as hypertension and diabetes. The user's visual field improvement effect may be increased through such the customization of the attribute of the visual object.

An attribute of a visual object output to a specific position on an output module may be expressed based on a weight corresponding to each output position of the output module. For example, a weight having a first value indicating a visual object having a first attribute and a weight having a second value indicating a visual object having a second attribute may correspond to a first position and a second position on the output module, respectively. In this specification, for convenience of description, it is described that a visual object has an attribute for providing a stronger stimulus to a user as the weight is greater, but is not limited thereto. It is indicated that a visual object has an attribute for providing a stronger stimulus to the user as the weight is smaller.

Depending on the attribute of the visual object, the visual field improvement effect may increase. For example, when a visual object having a specific spatial frequency or specific temporal frequency is output, the visual field improvement effect may increase.

According to an embodiment, the acquiring and evaluating of the user reaction (S1300) may include acquiring and evaluating a user's reaction corresponding to a visual perception task thus provided. For example, a device may acquire a user input corresponding to a user reaction from a user through an input module and may evaluate the user input through a controller to generate an evaluation result. Alternatively, the device may acquire a user input through an input module, may transmit the user input to a server through a communication module, and may receive an evaluation result evaluated by the server.

The evaluation result may mean indicating the user's task performance level for the visual perception task. Here, the user's task performance level may reflect the user's visual ability. For example, the user's task performance level may be expressed as a score or grade.

The evaluation result may be calculated to correspond to cells of a visual field map. Alternatively, the evaluation result may be calculated to correspond to an output position where the visual object is displayed in the output module.

Alternatively, the evaluation result may be calculated to correspond to the user's visual field area.

Referring to FIG. 8, because rotational directions of the first visual object 7 and the second visual object 8 are different from each other, an event that a user performs an reaction corresponding to the attribute mismatch may correspond to a correct answer. When the user performs a reaction corresponding to the correct answer (e.g., the user enters a user input corresponding to the attribute mismatch), a correct answer rate at a position where the second visual object 8 is displayed, and a correct answer rate in a cell corresponding to the position in a visual field area on the visual field map may increase. That fact that the correct answer rate is high may mean that a visual ability of the corresponding visual field area is good.

The acquiring and evaluating of the user reaction (S1300) may include updating visual ability information based on the evaluation result. According to an embodiment, the updating of the visual ability information based on the evaluation result may include generating visual ability information such as a visual field map based on the evaluation result or updating existing visual ability information based on the evaluation result. For example, a vision index indicating a visual ability better than a cell corresponding to a low correct answer rate may be assigned to a cell corresponding to a high correct answer rate. Alternatively, a vision score higher than (closer to 0) a cell corresponding to the low correct answer rate may be assigned to a cell corresponding to the high correct answer rate. Alternatively, a vision status indicating a status better than a cell corresponding to a low correct answer rate may be assigned to a cell corresponding to the high correct answer rate.

Here, it is described that the evaluation result is separated from visual ability information. However, the evaluation result itself may be visual ability information. For example, the evaluation result is calculated in a form of a visual field map.

As described above, a visual perception task may be provided based on the evaluation result. For example, the visual perception task of the next session may be provided based on the evaluation result of the previous session.

Depending on the evaluation result, the output position of the visual object may be determined. For example, a visual object may be displayed at a position corresponding to a visual field area where a visual ability is changed. Here, the visual field area where a visual ability is changed may mean a visual field area where the visual ability is improved or reduced.

The output frequency of the visual object may be determined depending on the evaluation result. For example, the output frequency of a visual object output to a position corresponding to a visual field area where the visual ability is changed may be changed. For example, the output frequency of a visual object output to a position corresponding to a visual field area having the reduced visual ability may increase. As another example, the output frequency of a visual object output to a position corresponding to a visual field area having improved visual ability may increase.

Depending on the evaluation result, the output order of the visual object may be determined.

Depending on the evaluation result, the attribute of the visual object may be determined. For example, the attribute of a visual object output to a position corresponding to a visual field area where visual ability is changed may be changed. For example, the attribute of a visual object displayed at a position corresponding to a visual field area with the reduced visual ability may be changed to provide a stronger stimulus or a weaker stimulus. As another example, the attribute of a visual object displayed at a position corresponding to a visual field area with the improved visual ability may be changed to provide a stronger stimulus or a weaker stimulus.

According to an embodiment, the providing of the visual perception task (S1200) may include providing a visual perception task in consideration of the vision index of an adjacent cell. Here, providing a visual perception task in consideration of the vision index of an adjacent cell may include outputting a visual object in consideration of the vision index of the adjacent cell.

Figure 16:
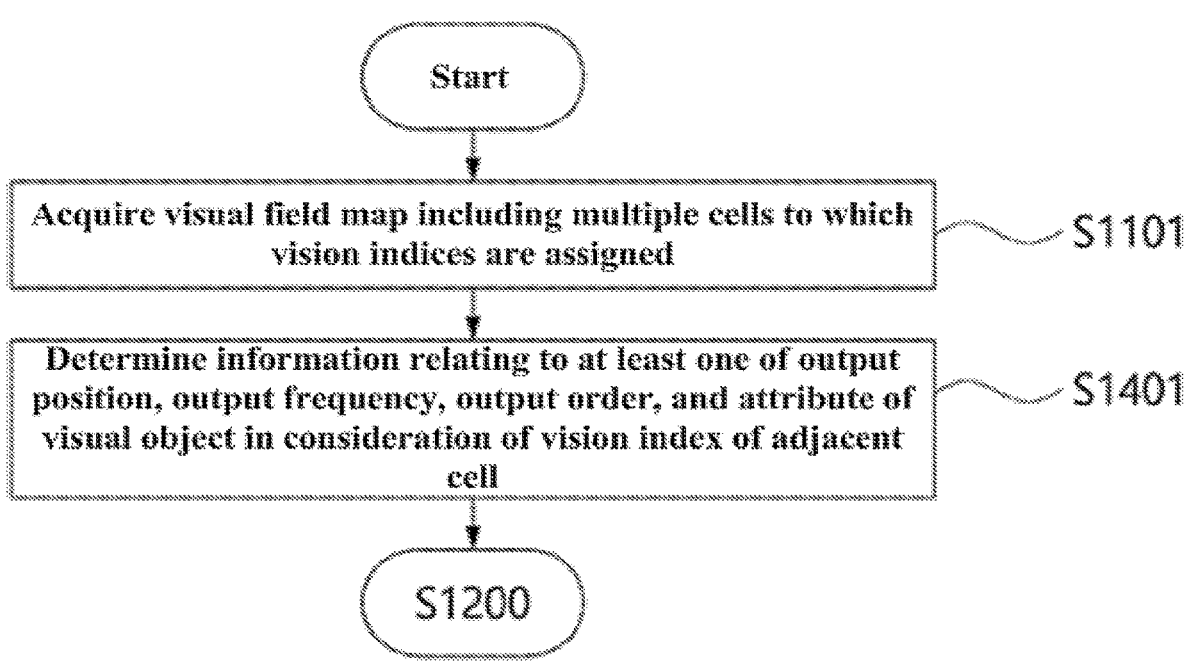
FIG. 16 is a diagram for describing determining information about at least one of an output position, an output frequency, an output order, and an attribute of a visual object in consideration of a vision index of an adjacent cell, according to an embodiment of the inventive concept.
Figure 17:
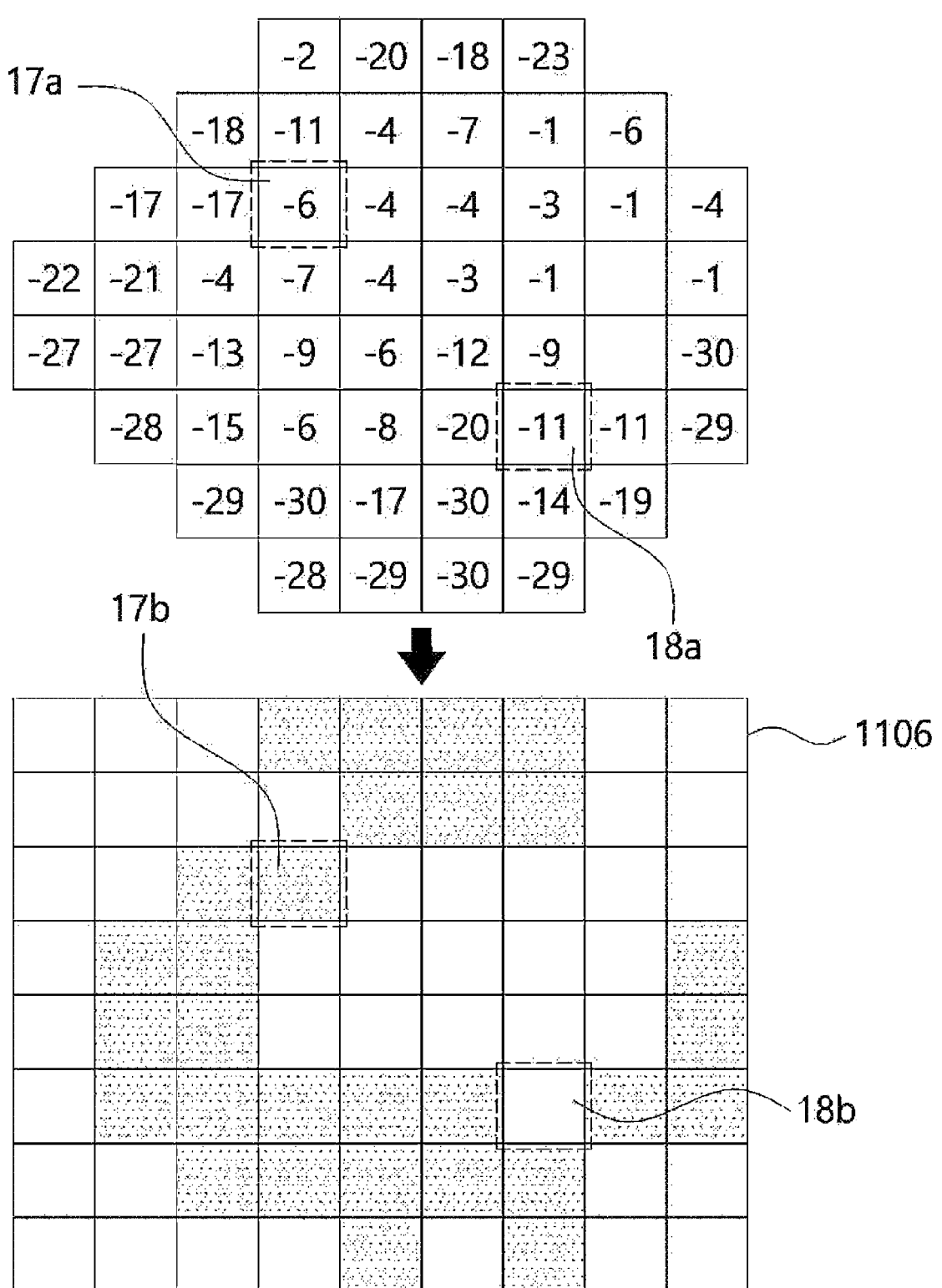
FIG. 17 is a diagram for describing determining information about at least one of an output position, an output frequency, an output order, and an attribute of a visual object in consideration of a vision index of an adjacent cell, according to an embodiment of the inventive concept.

FIGS. 16 and 17 are diagrams for describing determining information about at least one of an output position, an output frequency, an output order, and an attribute of a visual object in consideration of a vision index of an adjacent cell, according to an embodiment of the inventive concept.

First of all, referring to FIG. 16, according to an embodiment, a method for improving a visual ability by using visual perception learning may include acquiring a visual field map including multiple cells to which vision indices are assigned (S1101), and determining information about at least one of an output position, an output frequency, an output order, and an attribute of the visual object in consideration of the vision index of the adjacent cell (S1401).

The acquiring of the visual field map including the multiple cells to which vision indices are assigned (S1101) is an embodiment of acquiring visual ability information (S1100), and the description thereof is described above. Accordingly, additional descriptions will be omitted to avoid redundancy.

According to an embodiment, the determining of the information about the output position of the visual object (S1410) may include determining information about an output position of a visual object in consideration of a vision index of an adjacent cell.

According to an embodiment, the determining of the information about the output position of the visual object in consideration of the vision index of the adjacent cell may include determining an output position of a visual object in consideration of a difference between a vision index of a specific cell and a vision index of a cell adjacent to the specific cell. For example, when the difference in the vision index is not less than a predetermined grade or a value, a visual object may be output at a position on a display corresponding to the specific cell. Alternatively, when the difference in the vision index is included in the predetermined grade range or numerical range, a visual object may be output at a position on the display corresponding to the specific cell.

Next, referring to FIG. 17, a vision score difference between cells positioned at the top, bottom, left, and right of the specific cell may be calculated based on the specific cell. When one or more differences are greater than a predetermined value (e.g., 10 in FIG. 17), a visual object may be output at a position on the output module corresponding to the specific cell. For example, a vision score difference between a first cell 17a and a cell positioned on a left of the first cell 17a may be greater than or equal to 10 (i.e., 11). A visual object may be output at a first position 17b on an output module 1106 corresponding thereto. For example, a vision score difference between a second cell 18a and cells positioned on the top, bottom, left, and right of the second cell 18a may be smaller than 10. A visual object may not be output to a second position 18b on the output module 1106 corresponding thereto. In FIG. 17, for convenience of description, the position 17b where a visual object is output and the position 18*b* where a visual object is not output are expressed to have different patterns from each other. Moreover, in FIG. 17, limiting adjacent cells to cells positioned the top, bottom, left, and right is an example. Besides, the adjacent cells may be defined in various manners such as considering eight cells surrounding a specific cell as adjacent cells. For example, when cells adjacent to the second cell 18*a* are limited to eight cells surrounding the second cell 18*a*, a vision score difference between the second cell 18*a* and a cell positioned at a left bottom of the second cell 18*a* is 19. In this case, a visual object may be displayed at the second position 18*b*.

According to an embodiment, the determining of the information about the output frequency of the visual object (S1420) may include determining information about an output frequency of a visual object in consideration of a vision index of an adjacent cell.

According to an embodiment, the determining of the information about the output frequency of the visual object in consideration of the vision index of the adjacent cell may include determining an output frequency of a visual object in consideration of a difference between a vision index of a specific cell and a vision index of a cell adjacent to the specific cell. For example, it may be determined that the output frequency is high as a difference in the vision index is great. Alternatively, it may be determined that the output frequency is high compared to the rest when the vision index difference is included in a predetermined range. Referring to FIG. 17, a frequency at which a visual object is output at the first position 17*b* may be different from a frequency at which the visual object is output at the second position 18*b*.

According to an embodiment, the determining of the information about the output order of the visual object (S1430) may include determining information about an output order of a visual object in consideration of a vision index of an adjacent cell.

According to an embodiment, the determining of the information about the output order of the visual object in consideration of the vision index of the adjacent cell may include determining an output order of a visual object in consideration of a difference between a vision index of a specific cell and a vision index of a cell adjacent to the specific cell. For example, referring to FIG. 17, visual objects may be output at different time points from each other at the first position 17*b* and the second position 18*b*, respectively.

According to an embodiment, the determining of the information about the attribute of the visual object (S1440) may include determining information about an attribute of a visual object in consideration of a vision index of an adjacent cell.

According to an embodiment, the determining of the information about the attribute of the visual object in consideration of the vision index of the adjacent cell may include determining the information about the attribute of a visual object in consideration of a difference between a vision index of a specific cell and a vision index of a cell adjacent to the specific cell. For example, referring to FIG. 17, the attribute of the visual object displayed at the first position 17*b* may be different from the attribute of the visual object displayed at the second position 18*b*.

According to an embodiment, the providing of the visual perception task (S1200) may include providing a visual perception task in consideration of the position/direction of a visual field area. Here, providing the visual perception task in consideration of the position/direction of the visual field area may include outputting a visual object in consideration of the position/direction of the visual field area. People may generally use a lower visual field more than an upper visual field and a central visual field more than a peripheral visual field. When a target area is determined in consideration of the position/direction of a visual field area, the visual field improvement effect may be increased.

Figure 18:
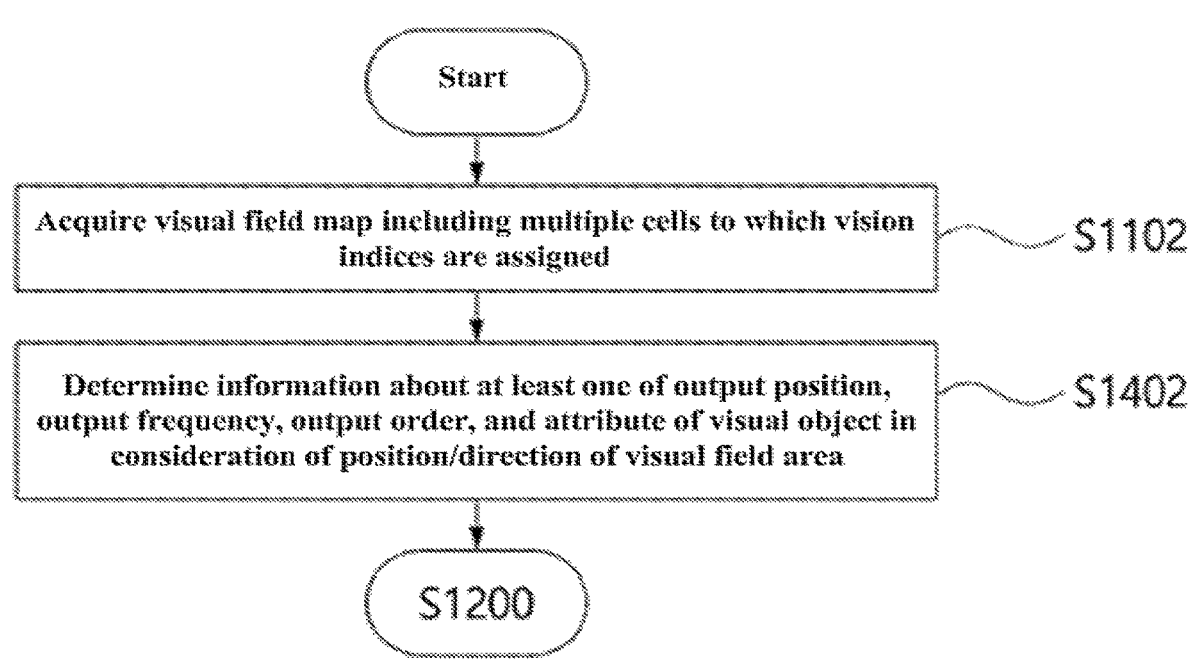
FIG. 18 is a diagram for describing determining information about at least one of an output position, an output frequency, an output order, and an attribute of a visual object in consideration of a position/direction of a visual field area, according to an embodiment of the inventive concept.
Figure 19:
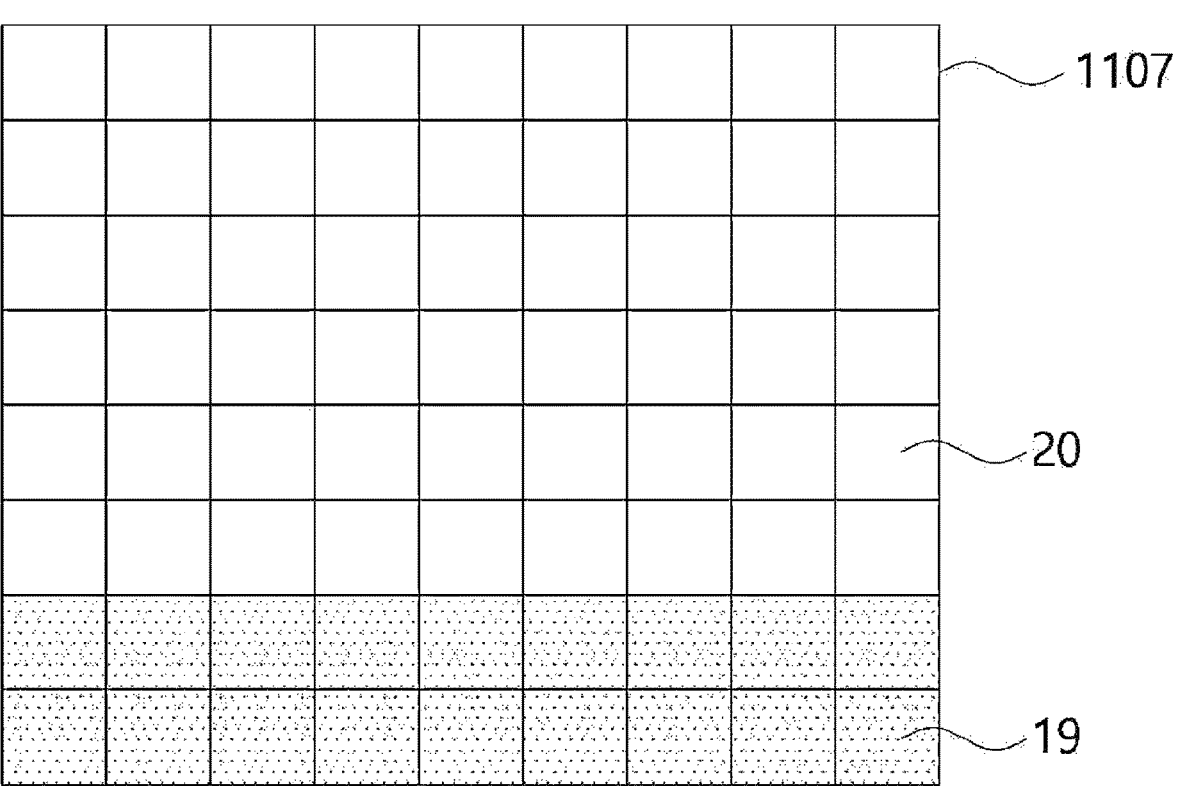
FIG. 19 is a diagram for describing determining information about at least one of an output position, an output frequency, an output order, and an attribute of a visual object in consideration of a position/direction of a visual field area, according to an embodiment of the inventive concept.

FIGS. 18 and 19 are diagrams for describing determining information about at least one of an output position, an output frequency, an output order, and an attribute of a visual object in consideration of a position/direction of a visual field area, according to an embodiment of the inventive concept.

First of all, referring to FIG. 18, according to an embodiment, a method for improving a visual ability by using visual perception learning may include acquiring a visual field map including multiple cells to which vision indices are assigned (S1102), and determining information about at least one of an output position, an output frequency, an output order, and an attribute of the visual object in consideration of a position/direction of a visual field area (S1402).

The acquiring of the visual field map including the cells to which vision indices are assigned (S1102) is an embodiment of acquiring visual ability information (S1100), and the description thereof is described above. Accordingly, additional descriptions will be omitted to avoid redundancy.

According to an embodiment, the determining of the information about the output position of the visual object (S1410) may include determining information about an output position of a visual object in consideration of a position/direction of a visual field area. For example, the determining of information about the output position of the visual object in consideration of the position/direction of the visual field area may determine to output the visual object at an output position corresponding to a first visual field area.

According to an embodiment, the determining of information about the output position of the visual object in consideration of the position/direction of the visual field area may determine to output the visual object at an output position corresponding to a lower visual field area. For example, referring to FIG. 19, a visual object may be output to an output position 19 of an output module 1107 corresponding to the lower visual field area.

According to another embodiment, the determining of information about the output position of the visual object in consideration of the position/direction of the visual field area may determine to output the visual object at an output position corresponding to a central visual field area.

According to still another embodiment, the determining of information about the output position of the visual object in consideration of the position/direction of the visual field area may determine to output the visual object at an output position corresponding to a macula.

According to an embodiment, the determining of the information about the output frequency of the visual object (S1420) may include determining information about an output frequency of a visual object in consideration of a position/direction of a visual field area. For example, the determining of information about the output frequency of the visual object in consideration of the position/direction of the visual field area may determine that an output frequency of a first position on an output module corresponding to a first visual field area is different from an output frequency of a second position on the output module corresponding to a second visual field area.

According to an embodiment, an output frequency at an output position corresponding to a lower visual field area may be greater than an output frequency at the other positions on the output module. For example, referring to FIG. 19, an output frequency of the visual object at the output position 19 on the output module 1107 corresponding to the lower visual field area may be greater than an output frequency at other positions 20.

According to another embodiment, an output frequency at an output position corresponding to the central visual field area may be greater than an output frequency at an output position corresponding to a peripheral visual field area.

According to still another embodiment, an output frequency at an output position corresponding to the macula may be greater than an output frequency at other positions on the output module.

According to an embodiment, the determining of the information about the output order of the visual object (S1430) may include determining information about an output order of a visual object in consideration of a position/direction of a visual field area. For example, the determining of information about the output order of the visual object in consideration of the position/direction of the visual field area may determine that an output order of a first position on an output module corresponding to a first visual field area is different from an output order of a second position on the output module corresponding to a second visual field area.

According to an embodiment, the determining of the information about the attribute of the visual object (S1440) may include determining information about an attribute of a visual object in consideration of a position/direction of a visual field area.

According to an embodiment, a visual object output at an output position corresponding to the lower visual field area may be determined to have an attribute for providing a stronger stimulus to a user than a visual object output at an output position corresponding to the remaining area.

According to another embodiment, a visual object output at an output position corresponding to the central visual field area may be determined to have an attribute for providing a stronger stimulus to the user than a visual object output at an output position corresponding to the peripheral visual field area.

According to still another embodiment, a visual object output at an output position corresponding to a macula may be determined to have an attribute for providing a stronger stimulus to a user than a visual object output at an output position corresponding to the remaining area.

According to an embodiment, the providing of the visual perception task (S1200) may include providing a visual perception task in consideration of a test result (hereinafter referred to as an "additional test result") obtained by eye and visual ability-related measurement equipment (hereinafter referred to as "additional measuring equipment") other than general visual field test equipment such as optic nerve imaging equipment, optic nerve optical coherence tomography equipment, and evoked potential testing equipment. Here, providing a visual perception task in consideration of the additional test result may be outputting a visual object in consideration of the additional test result.

A general perimetry measures a visual field through an input such as pressing a button based on whether a user sees an object such as a blinking light. Accordingly, because the subjective determination of the user is involved, it may be determined that the result measured by the additional measuring equipment indicates that a portion that appears normal is abnormal, or the result measured by the additional measuring equipment indicates that a portion that appears abnormal is normal. Accordingly, it is possible to provide a visual perception task or to output a visual object in consideration of both the general perimetry and the additional test result, thereby improving the accuracy of user's visual ability information and increasing the visual field improvement effect.

Figure 20:
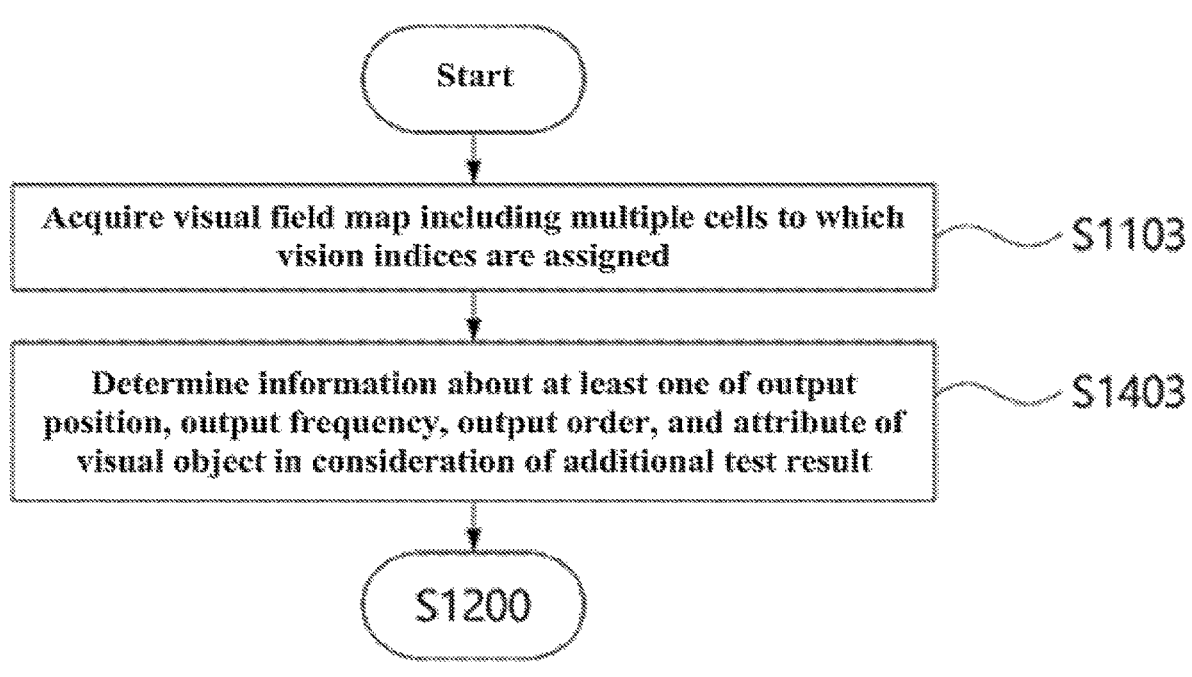
FIG. 20 is a flowchart for describing determining information about at least one of an output position, an output frequency, an output order, and an attribute of a visual object in consideration of an additional test result, according to an embodiment of the inventive concept.

FIG. 20 is a flowchart for describing determining information about at least one of an output position, an output frequency, an output order, and an attribute of a visual object in consideration of an additional test result, according to an embodiment of the inventive concept. Referring to FIG. 20, according to an embodiment, a method for improving a visual ability by using visual perception learning may include acquiring a visual field map including multiple cells to which vision indices are assigned (S1103), and determining information about at least one of an output position, an output frequency, an output order, and an attribute of the visual object in consideration of an additional test result (S1403).

The acquiring of the visual field map including the multiple cells to which vision indices are assigned (S1103) is an embodiment of acquiring visual ability information (S1100), and the description thereof is described above. Accordingly, additional descriptions will be omitted to avoid redundancy.

According to an embodiment, the determining of the information about the output position of the visual object (S1410) may include determining information about an output position of a visual object in consideration of an additional test result.

According to an embodiment, the output position of the visual object may be determined in consideration of at least one of a vision index and an additional test result. For example, when the additional test result indicates abnormality or visual field damages even though the vision index indicates normality, a visual object may be output at an output position corresponding thereto.

According to an embodiment, the determining of the information about the output frequency of the visual object (S1420) may include determining information about an output frequency of a visual object in consideration of an additional test result.

According to an embodiment, the output frequency of the visual object may be determined in consideration of at least one of a vision index and an additional test result. For example, an output frequency at an output position corresponding to an area where both the vision index and the additional test result indicate abnormality or visual field damages may be higher than an output frequency at an output position corresponding to the remaining area. Alternatively, an output frequency at an output position corresponding to an area where at least one of the vision index and the additional test result indicates abnormality or visual field damages may be higher than an output frequency at an output position corresponding to the remaining area.

According to an embodiment, the determining of the information about the output order of the visual object (S1430) may include determining information about an output order of a visual object in consideration of an additional test result. For example, the output order of the visual object may be determined in consideration of at least one of a vision index and an additional test result.

According to an embodiment, the determining of the information about the attribute of the visual object (S1440) may include determining information about an attribute of a visual object in consideration of an additional test result.

According to an embodiment, the attribute of the visual object may be determined in consideration of at least one of a vision index and an additional test result. For example, an attribute at an output position corresponding to an area where both the vision index and the additional test result indicate abnormality or visual field damages may be set to provide a user with a stronger stimulus than an attribute at an output position corresponding to the remaining area. Alternatively, an attribute at an output position corresponding to an area where at least one of the vision index and the additional test result indicates abnormality or visual field damages may be set to provide a user with a stronger stimulus than an attribute at an output position corresponding to the remaining area.

Figure 21:
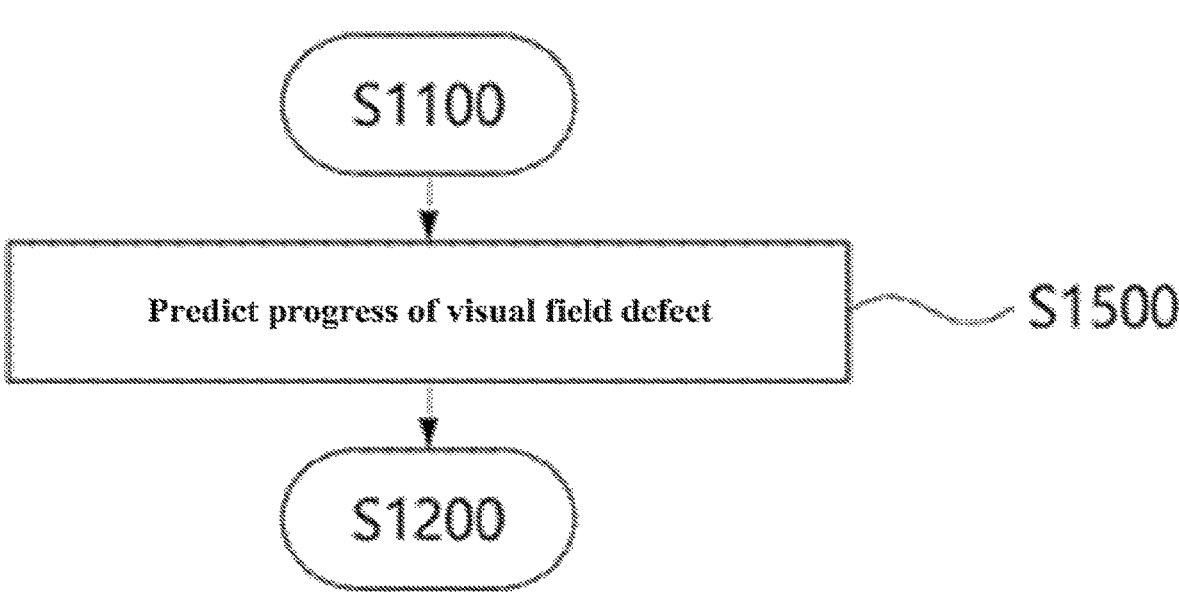
FIG. 21 is a diagram for describing predicting the progression of a visual field defect, according to an embodiment of the inventive concept.
Figure 22:
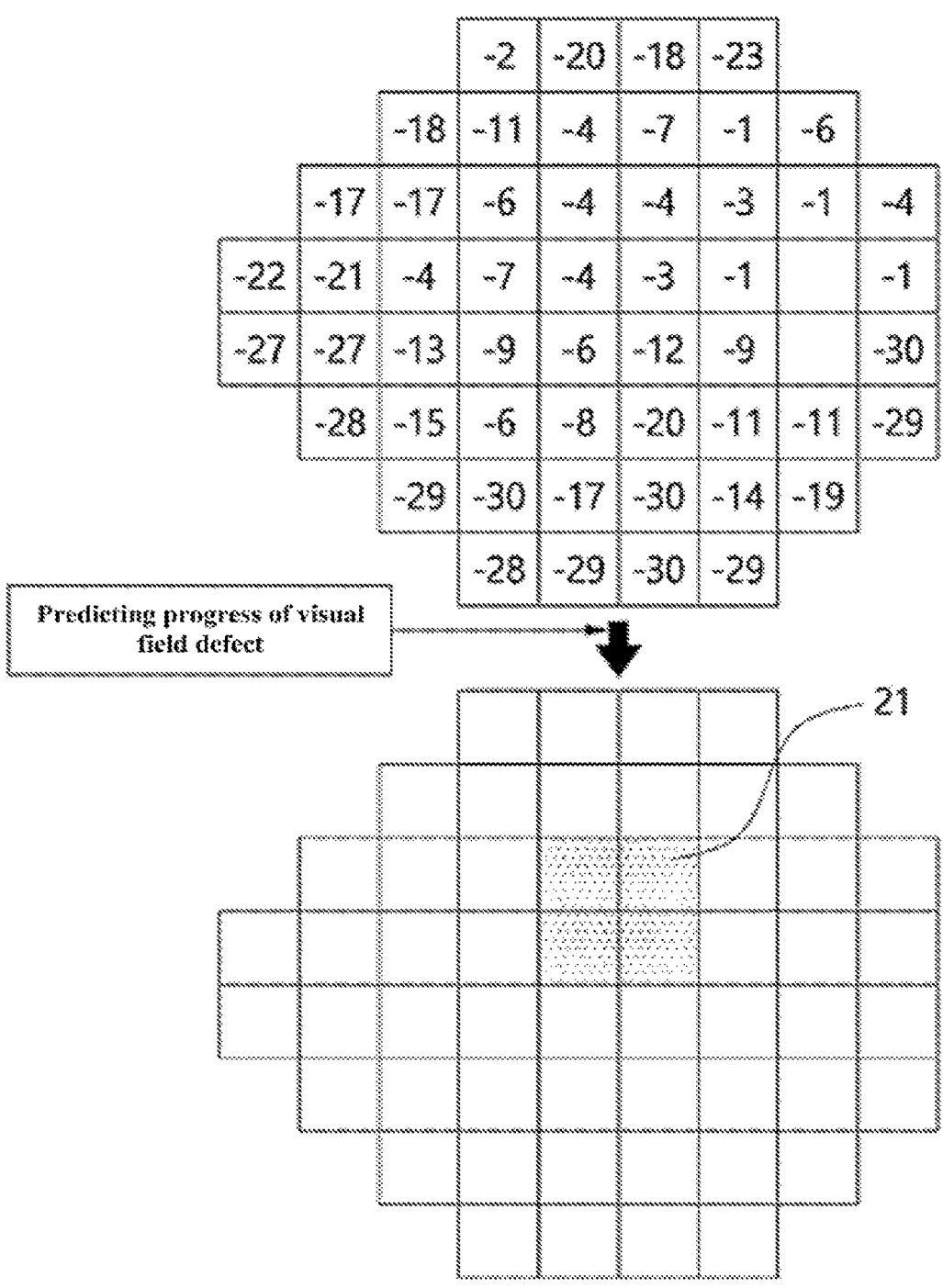
FIG. 22 is a diagram for describing predicting the progression of a visual field defect, according to an embodiment of the inventive concept.

FIGS. 21 and 22 are diagrams for describing predicting the progression of a visual field defect, according to an embodiment of the inventive concept.

First of all, referring to FIG. 21, a method for improving a visual ability by using visual perception learning according to an embodiment may include predicting the progress of a visual field defect (S1500). Here, the predicting of the progress of the visual field defect (S1500) may include predicting the progression of the visual field defect based on visual ability information.

According to an embodiment, the predicting of the progress of the visual field defect (S1500) may include predicting the visual ability information after a specific time interval. For example, a visual field map at the second time point, which is later than a first time point, may be predicted by predicting the progress of the visual field defect based on the visual field map (a vision index or visual ability information) at the first time point. Compared to the visual field map at the first time point, the visual field map at the second time point may include cells to which different vision indices are assigned. Alternatively, compared to the visual field map at the first time point, a visual field map at the second time point may include cells in each of which a vision index difference is greater than or equal to a predetermined value. In this specification, a vision index, visual field map, and visual ability information, which are measured through perimetry or other measurement equipment for distinction, will be referred to as a "measured vision index", a "measured visual field map", and "measured visual ability information", respectively. A vision index, a visual field map, and visual ability information, which are generated by predicting the progress of the visual field defect, will be referred to as an "expected vision index", an "expected visual field map", and "expected visual ability information", respectively.

According to another embodiment, the predicting of the progression of the visual field defect (S1500) may be predicting a cell, a visual field area, or an output position in which a visual field defect is expected to progress. For example, referring to FIG. 22, a cell 21 in which the progression of a visual field defect is expected may be predicted based on a visual field map (a vision index or visual ability information) at the first time point. Alternatively, it is possible to predict a visual field area or output position where the visual field defect is expected to progress, based on a visual field map (a vision index or visual ability information) at the first time point.

The providing of the visual perception task (S1200) according to an embodiment may include providing a visual perception task based on the progress of a predicted visual field defect.

According to an embodiment, the providing of the visual perception task (S1200) may include providing a visual perception task based on the expected ability information. This case is similar to the above-described providing the visual perception task (S1200), and thus the description thereof will be omitted to avoid redundancy.

According to another embodiment, the providing of the visual perception task (S1200) may include providing a visual perception task based on the measured visual ability information and the expected visual ability information. For example, a perceptual task may be provided based on a difference between the measured visual ability information and the expected visual ability information. For example, when the difference between the measured vision index and the expected vision index is a predetermined grade, is included in a predetermined numerical range, or is greater than or equal to a predetermined value, a visual object may be output at a position corresponding to the corresponding cell. Alternatively, the output frequency of a visual object output at the position may be greater than the output frequency of a visual object output at another position. Alternatively, the output order of a visual object output at the position may be different from the output order of a visual object output at another position. Alternatively, a visual object displayed at the position may have an attribute for providing a stronger stimulus than a visual object displayed at another position.

According to still another embodiment, the providing of the visual perception task (S1200) may include providing a visual perception task based on a cell, visual field area, or output position where the visual field defect is expected to progress. For example, a visual object may be output at the output position. Alternatively, the output frequency of a visual object output at the output position may be greater than the output frequency of a visual object output at another position. Alternatively, the output order of a visual object output at the output position may be different from the output order of a visual object output at another position. Alternatively, a visual object displayed at the output position may have an attribute for providing a stronger stimulus than a visual object displayed at another position.

The predicting of the progression of a visual field defect may be performed by using an artificial neural network.

The artificial neural network may be a type of algorithm created by imitating the structure of a human neural network, and may include one or more layers, each of which includes one or more nodes or neurons. Each of the nodes may be connected through a synapse. Data (input data) entered to the artificial neural network may be output (output data) via nodes through synapses, and information may be obtained through the synapses. For example, the artificial neural network may include an input layer for acquiring visual ability information (a vision index or a visual field map), a hidden layer, and an output layer outputting expected visual ability information (an expected vision index or an expected visual field map) or an expected visual field defect area.

The artificial neural network may include a convolution neural network (CNN) that extracts features by using filters, and a recurrent neural network (RNN) that has a structure in which an output of a node is fed back to an input. Various structures such as restricted Boltzmann machine (RBM), deep belief network (DBN), generative adversarial network (GAN), and relational networks (RN) may be applied to the artificial neural network. However, the artificial neural network is not limited thereto.

A training step is required before using an artificial neural network. Alternatively, it may be trained by using the artificial neural network. Hereinafter, a step of learning the artificial neural network is expressed as a learning step, and the step of using the artificial neural network is expressed as an inference step.

The artificial neural network may be trained through various methods such as supervised learning, unsupervised learning, reinforcement learning, and imitation learning.

Figure 23:
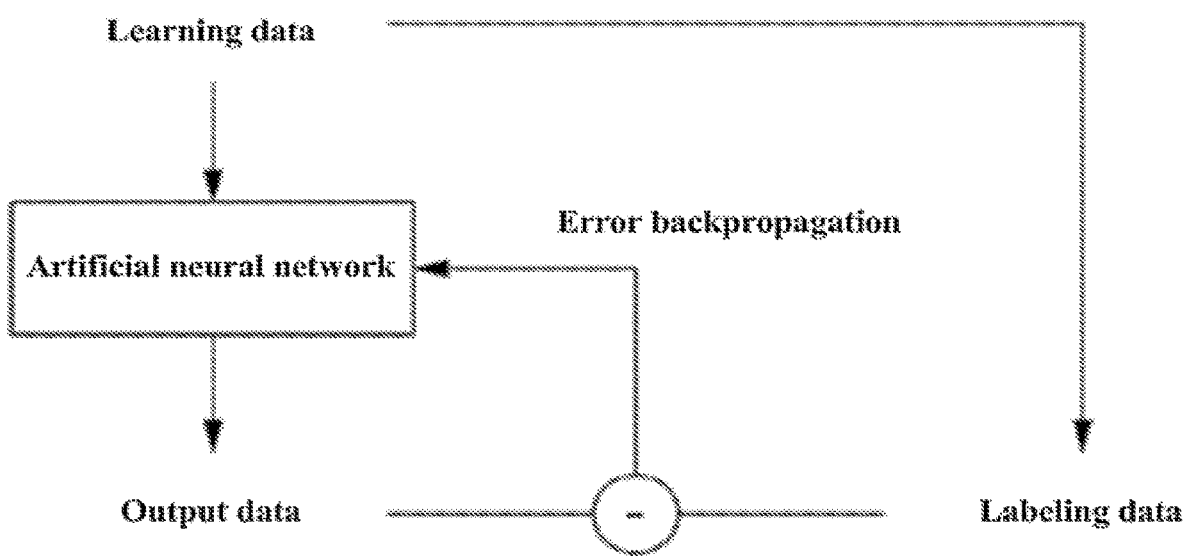
FIG. 23 is a diagram for describing a learning step of an artificial neural network, according to an embodiment of the inventive concept.

FIG. 23 is a diagram for describing a learning step of an artificial neural network, according to an embodiment of the inventive concept. FIG. 23 is an example of a learning step of an artificial neural network. An untrained artificial neural network may receive learning data or training data as input to output output data, may compare the output data with labeling data, and may train the artificial neural network through backpropagation of an error. Each of the learning data, the output data, and the labeling data may be visual ability information (a vision index or a visual field map). For example, the learning data may be visual ability information measured at a first time point; the labeling data may be visual ability information measured at a second time point later than the first time point; and the output data may be visual ability information at the second time point predicted by an artificial neural network. Alternatively, the learning data may be visual ability information measured at the first time point; the labeling data may be visual ability information that is determined to have progressed with a visual field defect at the second time point; and, the output data may be visual ability information predicted by the artificial neural network that the visual field defect has progressed. Alternatively, the learning data may be visual ability information measured at the first time point; the labeling data may be an area (or a cell or output position corresponding thereto) where it is determined that a visual field defect has progressed at the second time point; and, the output data may be an area (or a cell or output position corresponding thereto) where the artificial neural network predicts that the visual field defect has progressed.

Figure 24:
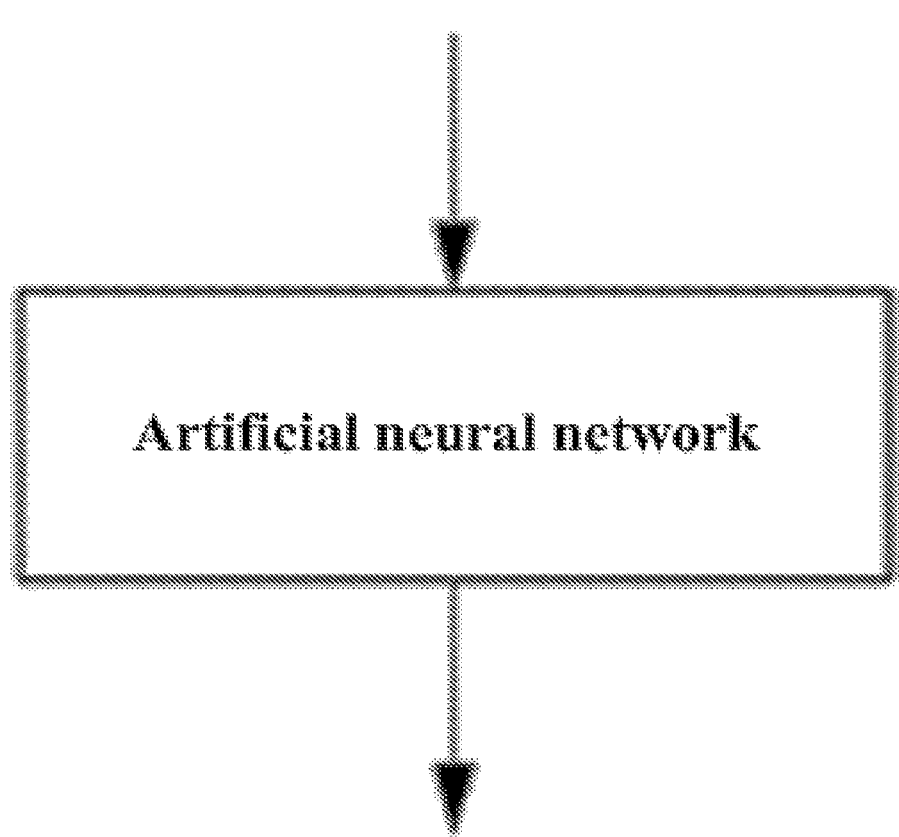
FIG. 24 is a diagram for describing an inference step of an artificial neural network, according to an embodiment of the inventive concept.

FIG. 24 is a diagram for describing an inference step of an artificial neural network, according to an embodiment of the inventive concept. FIG. 24 is an example of an inference step of an artificial neural network. A trained artificial neural network may receive input data and may output output data. Information capable of being inferred in the inference step may vary depending on information of learning data in a learning step. Moreover, the accuracy of output data may vary depending on a learning level of the artificial neural network. For example, as the learning level of the artificial neural network increases, the accuracy of the progression of a visual field defect predicted by the artificial neural network may increase.

In the above, a method for improving a visual ability mainly based on a piece of visual ability information is described. However, a person has both left eye and right eye, and there is a difference in visual ability between the left eye and the right eye. In diseases such as glaucoma, the progression of a visual field defect in the left eye is also different from the progression of a visual field defect in the right eye. Accordingly, there is a need to perform a method for improving a visual field in consideration of the left eye and the right eye together or separately.

Figure 25:
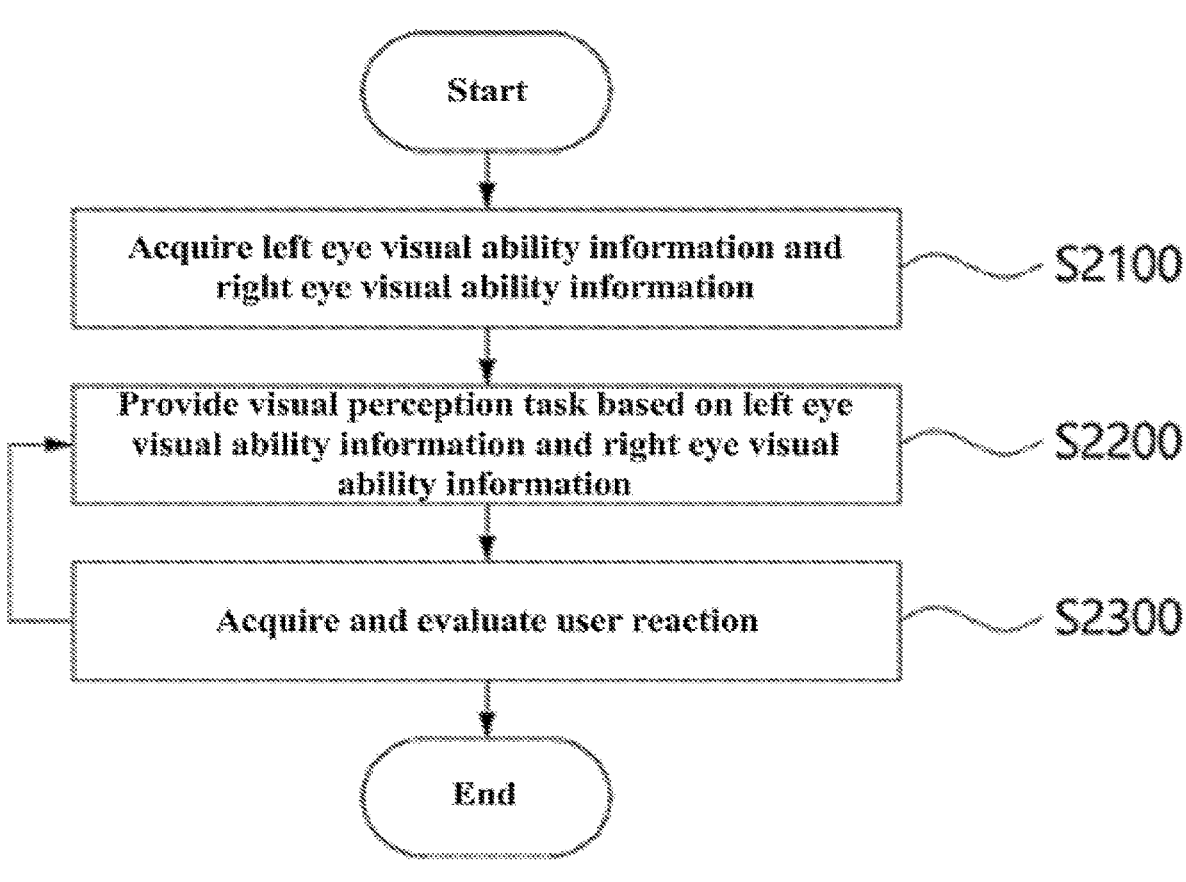
FIG. 25 is a flowchart for describing a method for improving a visual ability in consideration of binocular vision, according to an embodiment of the inventive concept.

FIG. 25 is a flowchart for describing a method for improving a visual ability in consideration of binocular vision, according to an embodiment of the inventive concept. Referring to FIG. 25, a method may include acquiring left eye visual ability information and right eye visual ability information (S2100), providing a visual perception task based on the left eye visual ability information and the right eye visual ability information (S2200), and acquiring and evaluating a user reaction (S2300). Hereinafter, a difference from a method for improving the above-mentioned visual ability will be mainly described. As long as it is not contradictory, the above-described method for improving the visual ability may be applied to the following as well.

The acquiring of the left eye visual ability information and the right eye visual ability information (S2100) may be an embodiment of acquiring visual ability information (S1100). The visual ability information may include the left eye visual ability information, which is information related to the visual ability of a user/patient's left eye, and the right eye visual ability information, which is information related to the visual ability of the user/patient's right eye. In general, the left eye visual ability information may be different from the right eye visual ability information. However, in some cases, the left eye visual ability information may be the same as the right eye visual ability information. The providing of the visual perception task based on the left eye visual ability information and the right eye visual ability information (S2200) may be an embodiment of the providing of the visual perception task (S1200).

A visual perception task may be provided to a left output unit and a right output unit at the same time point. For example, a visual object may be output at the same time point in the left output unit and the right output unit. In this case, visual objects output to the left output unit and the right output unit may be the same as or different from each other.

The left output unit and the right output unit may be provided with visual perception tasks at different time points from each other. For example, a visual perception task may be first provided to one of the left output unit and the right output unit, and then the visual perception task may be provided to the other one thereof.

According to an embodiment, the providing of the visual perception task based on the left eye visual ability information and the right eye visual ability information (S2200) may include providing a visual perception task separately in consideration of the left eye visual ability information and the right eye visual ability information. For example, the visual perception task may be provided to a left eye based on the left eye visual ability information, and the visual perception task may be provided to a right eye based on the right eye visual ability information. Alternatively, the visual object may be output to the left output unit based on the left eye visual ability information, and the visual object may be output to the right output unit based on the right eye visual ability information. In this case, a visual perception task provided to the left output unit may be different from a visual perception task provided to the right output unit.

According to an embodiment, information about at least one of an output position, an output frequency, an output order, and an attribute of a visual object output to the left output unit may be determined based on the left eye visual ability information, and information about at least one of an output position, an output frequency, an output order, and an attribute of a visual object output to the right output unit may be determined based on the right eye visual ability information.

Figure 26:
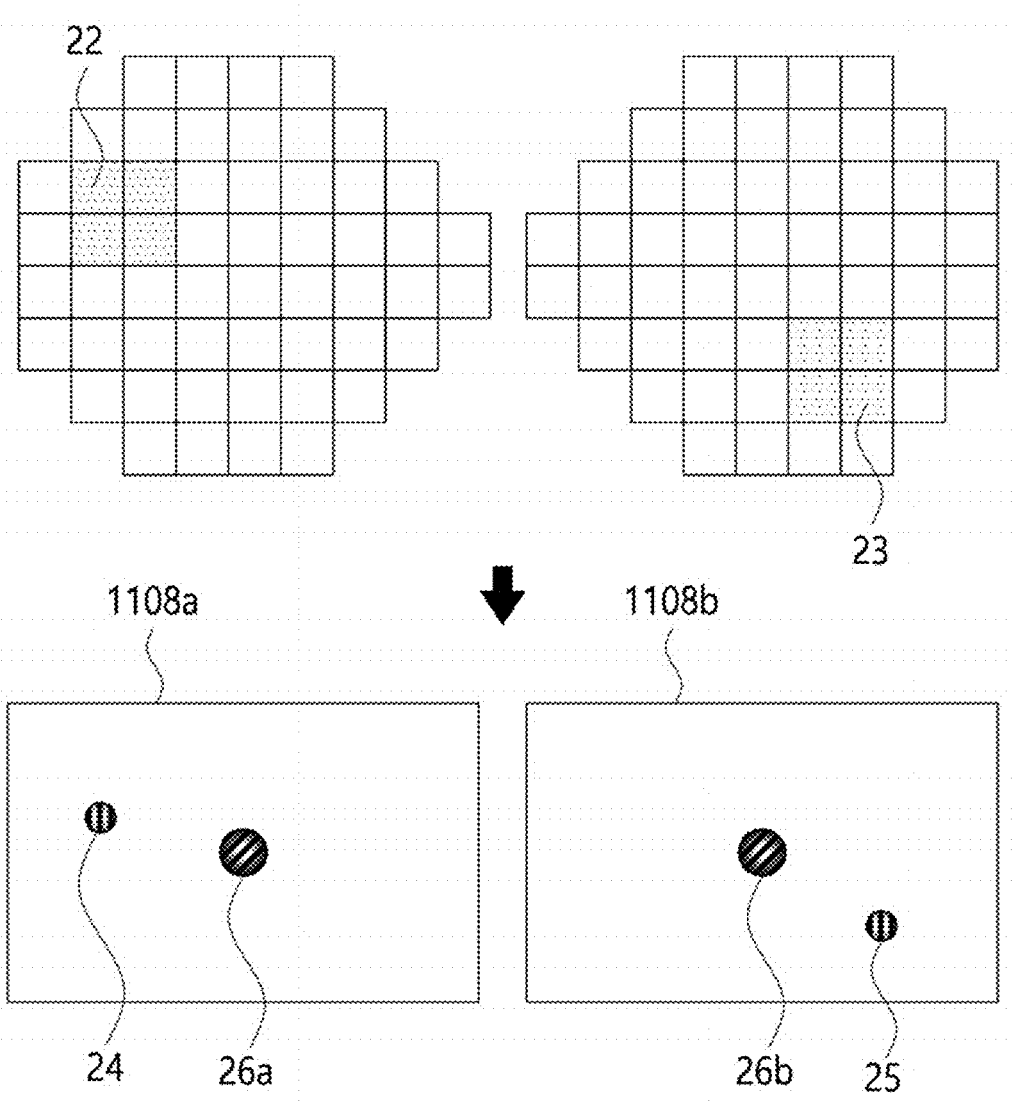
FIG. 26 is a diagram for describing providing a visual perception task based on left eye visual ability information and right eye visual ability information, according to an embodiment of the inventive concept.
Figure 27:
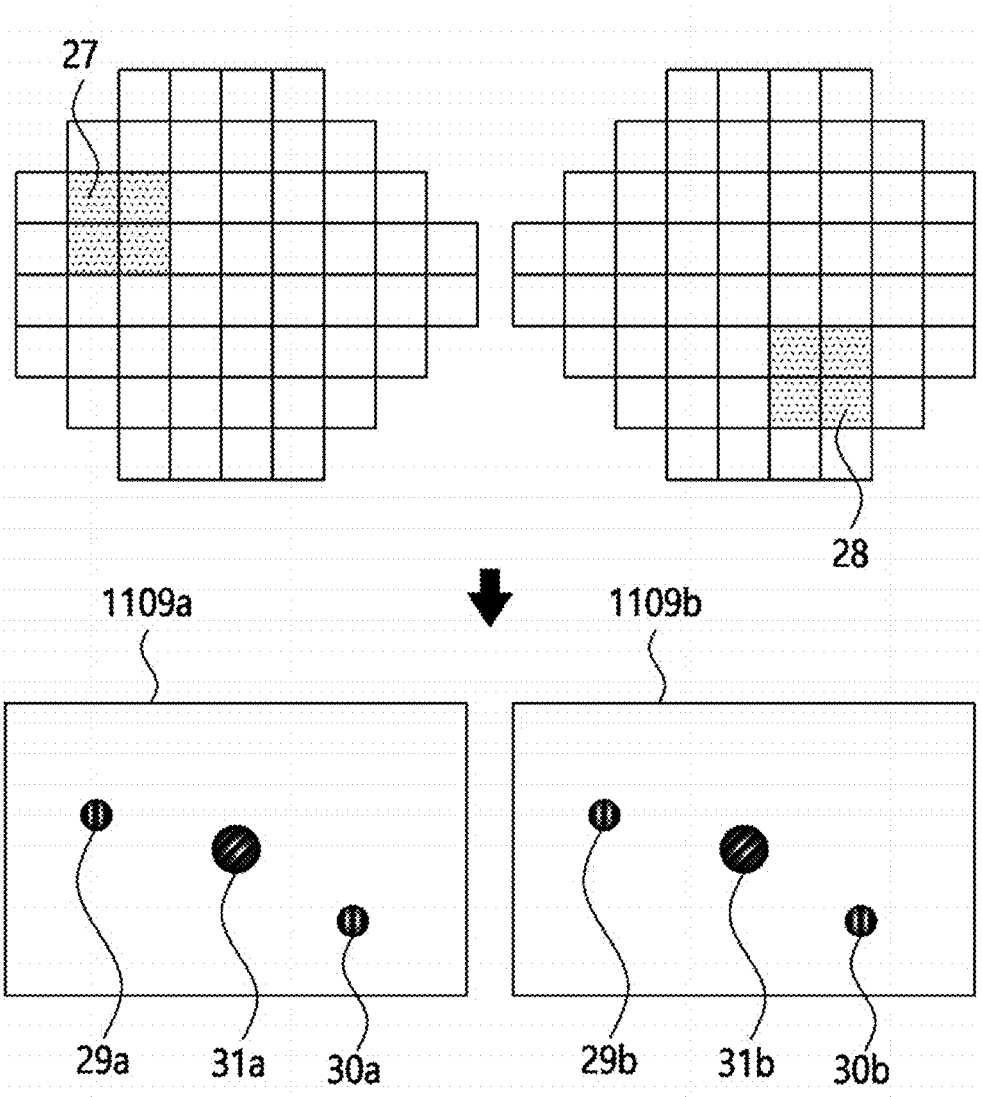
FIG. 27 is a diagram for describing providing a visual perception task in consideration of both left eye visual ability information and right eye visual ability information, according to an embodiment of the inventive concept.
Figure 28:
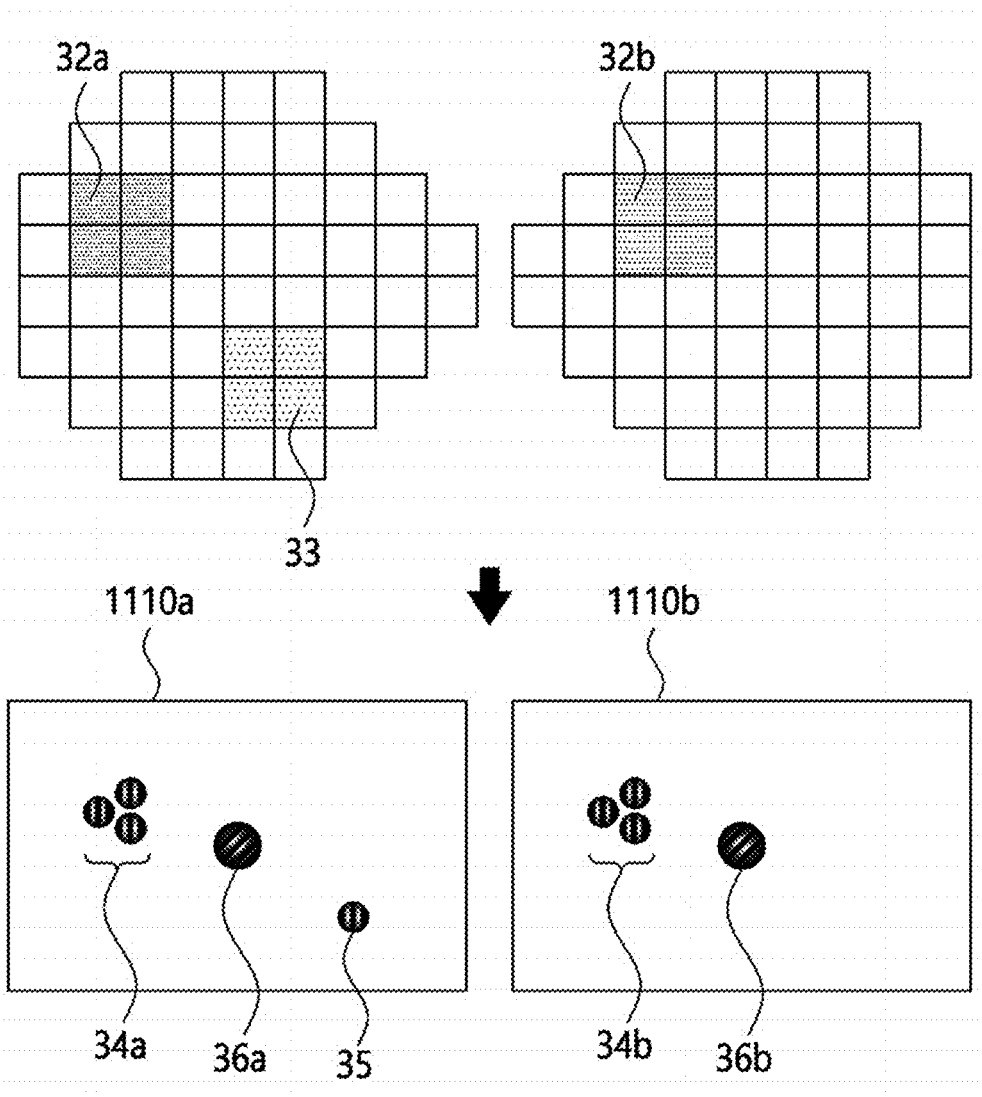
FIG. 28 is a diagram for describing providing a visual perception task in consideration of both left eye visual ability information and right eye visual ability information, according to an embodiment of the inventive concept.

FIGS. 26 to 28 are diagrams for describing providing a visual perception task based on left eye visual ability information and right eye visual ability information, according to an embodiment of the inventive concept.

First of all, referring to FIG. 26, as in the case where a visual object 24 is displayed at a position corresponding to a first target cell 22 of left eye visual ability information in a left output unit 1108a, a target position corresponding to the first target cell 22 may be determined.

As in the case where a visual object 25 is displayed at a position corresponding to a second target cell 23 of right eye visual ability information in a right output unit 1108b, a target position corresponding to the second target cell 23 may be determined. Here, each of the visual objects 24 and 25 may be a stimulus object. Visual objects 26a and 26b may be output at positions unrelated to visual ability information in the left output unit 1108a and the right output unit 1108b, respectively. Here, each of the visual objects 26a and 26b may be a central fixation object. Alternatively, each of the visual objects 26a and 26b may be a task object.

According to an embodiment, the providing of the visual perception task based on the left eye visual ability information and the right eye visual ability information (S2200) may include providing a visual perception task in consideration of both the left eye visual ability information and the right eye visual ability information. For example, a visual object may be output in consideration of both the left eye visual ability information and the right eye visual ability information. In this case, a visual perception task provided to the left output unit may be the same as or different from a visual perception task provided to the right output unit.

Next, referring to FIG. 27, a visual field area corresponding to a first target cell 27 of the left eye visual field map may be different from a visual field area corresponding to a second target cell 28 of the right eye visual field map. However, in this case, a target position (e.g., an output position of a visual object in a left output unit 1109a) may be determined in consideration of the second target cell 28. A target position (e.g., an output position of a visual object in a right output unit 1109b) may be determined in consideration of the first target cell 27. For example, the target position of the left output unit 1109a may include a first position 29a corresponding to the first target cell 27 and a second position 30a corresponding to the second target cell 28. Furthermore, a target position of the right output unit 1109b may include a third position 29b corresponding to the first target cell 27 and a fourth position 30b corresponding to the second target cell 28. In this case, visual perception tasks provided to the left output unit 1109a and the right output unit 1109b may be the same as each other. Moreover, the visual objects 29a, 29b, 30a, and 30b output to target positions of the left output unit 1109a and the right output unit 1109b may be stimulus objects. In addition, visual objects 31a and 31b may be output to the left output unit 1109a and the right output unit 1109b at positions unrelated to visual ability information. Here, each of the visual objects 31a and 31b may be a central fixation object.

When the visual field damage area of the left eye and the visual field damage area of the right eye are different from each other, a user may see the corresponding area by using one of both eyes. For example, an area corresponding to the visual field damage area of a left eye may be visible through the right eye, and an area corresponding to the visual field damage area of a right eye may be visible through the left eye. However, when the visual field damage area of the left eye and the visual field damage area of the right eye indicate to the same area as each other or overlap each other, the area may not be seen, thereby increasing discomfort. Accordingly, when the visual field damage area of the left eye and the visual field damage area of the right eye indicate the same area as each other, the corresponding area may be preferentially trained. Accordingly, the visual field improvement effect may also increase.

According to an embodiment, an area where the visual field damage area of the left eye and the visual field damage area of the right eye overlap each other may be determined as a target area. For example, when both the vision indices of the first cell of the left eye visual field map and the second cell of the right eye visual field map indicate a visual field defect/visual field damage, a first position on the left output unit corresponding to the first cell and a second position on the right output unit corresponding to the second cell may be determined as target positions. Alternatively, when a vision score of each of the first cell of the left eye visual field map and the second cell of the right eye visual field map corresponding to each other are less than a predetermined value or are included in a specific range, a first position on the left output unit corresponding to the first cell and a second position on the right output unit corresponding to the second cell may be determined as target positions. Alternatively, when each of vision statuses of each of the first cell of the left eye visual field map and the second cell of the right eye visual field map indicates a dysfunctional status, one indicates a disabled status, and the other indicates a dead status, a first position on the left output unit corresponding to the first cell and a second position on the right output unit corresponding to the second cell may be determined as target positions.

Next, referring to FIG. 28, the left eye visual field map and the right eye visual field map may correspond to the same visual field area as each other and may include first cells 32a and 32b indicating visual field damages. The first cells 32a and 32b may be determined as target cells. Positions 34a and 34b on the output modules 1110a and 1110b corresponding to the first cells 32a and 32b may be determined as target positions. Each of visual field areas corresponding to the first cells 32a and 32b may be determined as a target area. Furthermore, a cell of the right eye visual field map corresponding to the left eye visual field map may indicate a normal state. On the other hand, the left eye visual field map may include a second cell 33 indicating visual field damages. The second cell 33 may also be determined as a target cell. However, the training priority of the first cells 32a and 32b may be high. In this case, a visual field area corresponding to each of the first cells 32a and 32b may be referred to as a "main target area". An output frequency of a visual object at an output position corresponding to the main target area may be higher than an output frequency at positions corresponding to the remaining target areas. A visual object 34a output at an output position corresponding to the main target area may provide a stronger stimulus than a visual object 34b output at a position corresponding to another target area. As a non-limiting example, referring to FIG. 28, a larger number of visual objects may be displayed at the main target position than at another target position. Besides, visual objects 36a and 36b may be output at positions unrelated to visual ability information in the left output unit 1110a and the right output unit 1110b, respectively. Moreover, each of the visual objects 36a and 36b may be a central fixation object.

The acquiring and evaluating of the user reaction (S2300) according to an embodiment may be an embodiment of the above-described acquiring and evaluating a user reaction (S1300).

The user reaction may include a reaction (a reaction corresponding to a left eye) corresponding to the left eye and a reaction (a reaction corresponding to a right eye) corresponding to the right eye. For example, the reaction corresponding to the left eye may be a reaction related to a visual perception task provided to the left output unit, and the reaction corresponding to the right eye may be a reaction related to a visual perception task provided to the right output unit. Alternatively, the reaction corresponding to the left eye may be a reaction related to a visual object displayed on only the left output unit and a visual object displayed on both the left output unit and the right output unit. The reaction corresponding to the right eye may be a reaction related to a visual object displayed on only the right output unit and a visual object displayed on both the right output unit and the left output unit.

The visual ability of the left eye may be evaluated based on the left eye corresponding reaction. The visual ability of the right eye may be evaluated based on the right eye corresponding reaction. The visual ability of the left eye may be evaluated based on the reaction related to a visual object displayed on only the left output unit and a visual object displayed on both the right output unit and the left output unit. The visual ability of the right eye may be evaluated based on the reaction related to a visual object displayed on only the right output unit and a visual object displayed on both the right output unit and the left output unit. Here, the visual ability may be evaluated in consideration of the reaction related to the visual object displayed on a single output unit and the reaction related to the visual object displayed on both output units at different ratios/weights from each other. For example, the visual ability may be evaluated in consideration of the reaction related to the visual object displayed on a single output unit at a higher ratio/weight than the reaction related to the visual object displayed on both output units.

A method according to the embodiment may be implemented in a form of program instructions capable of being executed through various computing means to be recorded on a computer-readable medium. The computer-readable medium may also include program instructions, data files, data structures, or a combination thereof. The program instructions recorded in the media may be designed and configured especially for the example embodiments or be known and available to those skilled in computer software. The computer-readable medium may include a hardware device, which is specially configured to store and execute program instructions, such as magnetic media (e.g., a hard disk drive and a magnetic tape), optical recording media (e.g., CD-ROM and DVD), magneto-optical media (e.g., a floptical disk), read only memories (ROMs), random access memories (RAMs), and flash memories. Examples of computer programs include not only machine language codes created by a compiler, but also high-level language codes that are capable of being executed by a computer by using an interpreter or the like. The described hardware devices may be configured to act as one or more software modules to perform the operations of the above-described embodiments, or vice versa.

Various embodiments according to an embodiment of the inventive concept may be implemented as software including one or more instructions stored in a storage medium (e.g., a memory) readable by a machine. For example, the processor of a machine may call at least one instruction of the stored one or more instructions from a storage medium and then may execute the at least one instruction. This enables the machine to operate to perform at least one function depending on the called at least one instruction. The one or more instructions may include a code generated by a complier or a code executable by an interpreter. The machine-readable storage medium may be provided in the form of a non-transitory storage medium. Herein, 'non-transitory' just means that the storage medium is a tangible device and does not include a signal (e.g., electromagnetic waves), and this term does not distinguish between the case where data is semipermanently stored in the storage medium and the case where the data is stored temporarily. For example, the 'non-transitory storage medium' may include a buffer in which data is temporarily stored.

According to an embodiment, a method according to various embodiments disclosed in the specification may be provided to be included in a computer program product. The computer program product may be traded between a seller and a buyer as a product. The computer program product may be distributed in the form of a machine-readable storage medium (e.g., compact disc read only memory (CD-ROM)) or may be distributed (e.g., downloaded or uploaded), through an application store (e.g., PlayStore™), directly between two user devices (e.g., smartphones), or online. In the case of on-line distribution, at least part of the computer program product (e.g., a downloadable app) may be at least temporarily stored in the machine-readable storage medium such as the memory of a manufacturer's server, an application store's server, or a relay server or may be generated temporarily. Although an embodiment of the inventive concept are described with reference to the accompanying drawings, it will be understood by those skilled in the art to which the inventive concept pertains that the inventive concept may be carried out in other detailed forms without changing the scope and spirit or the essential features of the inventive concept. Therefore, the embodiments described above are provided by way of example in all aspects, and should be construed not to be restrictive.

According to an embodiment of the inventive concept, a visual ability may be improved by using visual perception learning.

Moreover, patients suffering from a visual field disorder may be provided with training for improving a visual ability by using visual perception learning.

Furthermore, the effect of visual perception learning may be increased by adjusting a visual perception task depending on a patient's visual ability.

While the inventive concept has been described with reference to embodiments, it will be apparent to those skilled in the art that various changes and modifications may be made without departing from the spirit and scope of the inventive concept. Therefore, it should be understood that the above embodiments are not limiting, but illustrative.

What is claimed is:

1. A device for providing visual perception training, the device comprising:

a display module; and a controller configured to acquire target areas corresponding to a first cell and a second cell of a visual field map of a patient, and to provide a visual perception task to the target areas, wherein, in the providing of the visual perception task, the controller is configured to:

display, through the display module, a task object for receiving a response of the patient and fixing a central visual field of the patient, on a central area of the display module;

display, through the display module, a first stimulus object and a second stimulus object at stimulus positions corresponding to the target areas; and acquire the response of the patient related to the task object, wherein the stimulus positions are positioned at a periphery of the task object, wherein the visual field map includes a plurality of cells to which vision indices reflecting a vision score of the patient are assigned, wherein a higher vision score indicates better visual ability, wherein the stimulus positions correspond to the first cell and the second cell to which the vision score included in a specific numerical range are assigned, and wherein a first cell assigned with a low vision score has a greater temporal output frequency of flickering of one or more stimulus objects in the first cell, than a temporal output frequency of flickering of one or more stimulus objects in a second cell assigned with a high vision score.

2. The device of claim 1, wherein the display module includes a left display unit and a right display unit, and wherein the controller is further configured to:

display the first stimulus object at at least one stimulus position of the stimulus positions, corresponding to the first cell, through the left display unit; and display the second stimulus object at at least one stimulus position of the stimulus positions, corresponding to the second cell, through the right display unit.

3. The device of claim 1, wherein the controller is configured to:

provide the patient with the visual perception task by displaying the task object during a specific time through the display module; and display a stimulus object during only a partial time of the specific time.

4. The device of claim 1, wherein the controller is further configured to display the first stimulus object at a first time point, and display the second stimulus at a second time point that is different from the first time point.

5. The device of claim 1, wherein at least one of the task object, the first stimulus cell, and the second stimulus object is a gabor.

6. The device of claim 5, wherein at least one of the first stimulus object and the second stimulus object is the gabor having a spatial frequency of 0.1 to 1 cycle/degree.

7. The device of claim 1, wherein at least one of the first stimulus object and the second stimulus object is output while flickering at a predetermined temporal frequency, and wherein the temporal frequency is 10 to 50 Hz.

8. The device of claim 1, wherein the response of the patient is associated with an attribute of the task object.

9. The device of claim 8, wherein the attribute includes at least one of a rotation direction and pattern orientation of the task object.

10. A method for improving a visual ability by using visual perception learning, the method comprising:

acquiring target areas corresponding to a first cell and a second cell of a visual field map of a patient; and providing a visual perception task to the target areas, wherein the providing of the visual perception task includes:

displaying a task object for receiving a response of the patient and fixing a central visual field of the patient;

displaying a first stimulus object and a second stimulus object at stimulus positions corresponding to the target areas; and acquiring the response of the patient related to the task object, wherein the stimulus positions are positioned at a periphery of the task object, wherein the visual field map includes a plurality of cells to which vision indices reflecting a vision score of the patient are assigned, wherein a higher vision score indicates better visual ability, wherein the stimulus positions correspond to the first cell and the second cell to which the vision score included in a specific numerical range are assigned, and wherein a first cell assigned with a low vision score has a greater temporal output frequency of flickering of one or more stimulus objects in the first cell, than a temporal output frequency of flickering of one or more stimulus objects in a second cell assigned with a high vision score.

11. The method of claim 10, wherein attributes of the first stimulus object and the second stimulus object are determined based on a vision index.

12. The method of claim 10, wherein the displaying of the first stimulus object and the second stimulus object comprises: displaying the first stimulus object at a first time point; and displaying the second stimulus object at a second time point that is different from the first time point.

13. The method of claim 10, wherein at least one of the task object, the first stimulus object, and the second stimulus object is a gabor.

14. The method of claim 13, wherein at least one of the first stimulus object and the second stimulus object is a gabor having a spatial frequency of 0.1 to 1 cycle/degree.

15. A non-transitory computer-readable recording medium recorded with a program for executing the method of claim 10.

* * * * *